US009993437B2

(12) United States Patent
Liong et al.

(10) Patent No.: US 9,993,437 B2
(45) Date of Patent: Jun. 12, 2018

(54) MESOPOROUS SILICA NANOPARTICLES FOR BIOMEDICAL APPLICATIONS

(75) Inventors: Monty Liong, Los Angeles, CA (US); Jie Lu, Los Angeles, CA (US); Fuyuhiko Tamanoi, Los Angeles, CA (US); Jeffrey I. Zink, Sherman Oaks, CA (US); Andre Nel, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 12/746,375

(22) PCT Filed: Dec. 8, 2008

(86) PCT No.: PCT/US2008/013476
§ 371 (c)(1),
(2), (4) Date: Jun. 4, 2010

(87) PCT Pub. No.: WO2009/078924
PCT Pub. Date: Jun. 25, 2009

(65) Prior Publication Data
US 2010/0255103 A1 Oct. 7, 2010

Related U.S. Application Data

(60) Provisional application No. 60/996,827, filed on Dec. 6, 2007.

(51) Int. Cl.
| A61K 9/14 | (2006.01) |
| A61K 9/51 | (2006.01) |
| A61K 9/50 | (2006.01) |
| A61K 31/337 | (2006.01) |
| A61K 31/4375 | (2006.01) |
| A61K 49/00 | (2006.01) |
| A61K 49/18 | (2006.01) |
| B82Y 5/00 | (2011.01) |

(52) U.S. Cl.
CPC .......... *A61K 9/5115* (2013.01); *A61K 9/5094* (2013.01); *A61K 31/337* (2013.01); *A61K 31/4375* (2013.01); *A61K 49/0002* (2013.01); *A61K 49/0043* (2013.01); *A61K 49/0052* (2013.01); *A61K 49/0093* (2013.01); *A61K 49/183* (2013.01); *B82Y 5/00* (2013.01)

(58) Field of Classification Search
None
See application file for complete search history.

(56) References Cited

U.S. PATENT DOCUMENTS

| 5,622,684 A | 4/1997 | Pinnavaia et al. |
| 6,615,855 B2 | 9/2003 | Lopez et al. |
| 6,755,621 B2 | 6/2004 | Lopez et al. |
| 6,767,531 B2 | 7/2004 | Fritzberg et al. |
| 6,902,806 B2 | 6/2005 | Fujiwara et al. |
| 6,913,825 B2 | 7/2005 | Ostafin et al. |
| 6,929,636 B1 | 8/2005 | von Alten |
| 7,163,658 B2 | 1/2007 | Bension |
| 7,258,874 B2 | 8/2007 | Barbe et al. |
| 7,354,602 B2 | 4/2008 | Barbe et al. |
| 7,354,603 B2 | 4/2008 | Barbe et al. |
| 7,357,948 B2 | 4/2008 | Barbe et al. |
| 7,563,451 B2 | 7/2009 | Lin et al. |
| 2003/0152759 A1 | 8/2003 | Chao et al. |
| 2004/0076681 A1 | 4/2004 | Dennis et al. |
| 2005/0130167 A1 | 6/2005 | Bao et al. |
| 2006/0154069 A1 | 7/2006 | Lin et al. |
| 2006/0216239 A1 | 9/2006 | Zhang et al. |
| 2007/0151038 A1 | 7/2007 | Lai et al. |
| 2008/0031960 A1 | 2/2008 | Wilson et al. |
| 2008/0107598 A1 | 5/2008 | Yang et al. |
| 2008/0175992 A1 | 7/2008 | Plieth et al. |
| 2008/0206146 A1 | 8/2008 | Akhtari et al. |
| 2009/0196826 A1 | 8/2009 | Gao et al. |
| 2010/0016610 A1 | 1/2010 | Keinan |
| 2010/0143263 A1 | 6/2010 | Cheon et al. |
| 2010/0284924 A1 | 11/2010 | Zink et al. |
| 2010/0310465 A1 | 12/2010 | Zink et al. |

(Continued)

FOREIGN PATENT DOCUMENTS

| KR | 10-0924786 B1 | 11/2009 |
| WO | WO-2006/015757 | 2/2006 |

(Continued)

OTHER PUBLICATIONS

Radu, D. R.; Lai, C.; Huang, J.; Shu, X.; Lin, V. Fine-tuning the degree of organic functionalization of mesoporous silica nanosphere materials via an interfacially designed co-condensation method. Chem. Commun., 2005, 1264-1266.*
Trewyn, B. G.; Slowing, I. I.; Giri, S.; Chen, H.; Lin, V. S. Synthesis and Functionalization of a Mesoporous Silica Nanoparticle Based on the Sol-Gel Process and Applications in Controlled Release. Acc. Chem. Res. 2007, 40, 846-853.*
International Search Report and Written Opinion for PCT/US08/13476.
Zhou et al, "Zirconium Phosphonate-Modified Porous Silicon for Highly Specific Capture of Phosphopeptides and MALDI-TOF MS Analysis," Journal of Proteome Research, vol. 5, pp. 2431-2437, Sep. 2006.
Gupta et al. "Synthesis and surface engineering of iron oxide nanoparticles for biomedical applications," Biomaterials, 2005, vol. 26, pp. 3995-4021.

(Continued)

*Primary Examiner* — Jessica Worsham
(74) *Attorney, Agent, or Firm* — Tom Hunter; Weaver Austin Villeneuve & Sampson LLP

(57) ABSTRACT

A submicron structure includes a silica body defining a plurality of pores that are suitable to receive molecules therein, the silica body further defining an outer surface between pore openings of the plurality of pores; and a plurality of anionic molecules attached to the outer surface of the silica body. The anionic molecules provide hydrophilicity to the submicron structure and are suitable to provide repulsion between other similar submicron structures, and the submicron structure has a maximum dimension less than one micron.

23 Claims, 16 Drawing Sheets

(56) References Cited

U.S. PATENT DOCUMENTS

| | | | |
|---|---|---|---|
| 2011/0104073 A1 | 5/2011 | Zeng et al. |
| 2011/0268791 A1 | 11/2011 | Liu et al. |
| 2012/0021034 A1 | 1/2012 | Zink et al. |
| 2012/0207795 A1 | 8/2012 | Zink et al. |
| 2013/0046274 A1 | 2/2013 | Zink et al. |
| 2016/0008283 A1 | 1/2016 | Nel et al. |
| 2017/0095418 A1 | 4/2017 | Zink et al. |

FOREIGN PATENT DOCUMENTS

| | | |
|---|---|---|
| WO | WO 2006/032136 A1 | 3/2006 |
| WO | WO 2007/010574 A1 | 1/2007 |
| WO | WO 2007/015105 A2 | 2/2007 |
| WO | WO-2007/131286 | 11/2007 |
| WO | WO 2009/064964 A2 | 5/2009 |
| WO | WO 2009/078924 A2 | 6/2009 |
| WO | WO 2009/094568 A1 | 7/2009 |
| WO | WO 2009/094580 A2 | 7/2009 |
| WO | WO 2009/097439 A1 | 8/2009 |
| WO | WO 2010/071831 A2 | 6/2010 |
| WO | WO 2010/078569 A2 | 7/2010 |
| WO | WO 2012/009448 A2 | 1/2012 |
| WO | WO 2013/012891 A1 | 1/2013 |
| WO | WO 2014/138278 A1 | 9/2014 |

OTHER PUBLICATIONS

Georganopoulou, et al., "Nanoparticle-Based Detection in Cerebral Spinal Fluid of a Soluble Pathogenic Biomarker for Alzheimer's Disease," Proc. Natl. Acad. Sci. USA (2005), 102, 2273-2276.

Gao, et al., "In Vivo Cancer Targeting and Imaging with Semiconductor Quantum Dots," Nat. Biotechnol. (2004), 22, 969-976.

Wu et al., "Immunofluorescent Labeling of Cancer Marker Her2 and Other Cellular Targets with Semiconductor Quantum Dots," Nat. Biotechnol. (2002), 21, 41-46.

Lee, et al., "Artificially Engineered Magnetic Nanoparticles for Ultra-Sensitive Molecular Imaging," Nat. Med. (2007), 13, 95-99. (Published online Dec. 24, 2006).

Na et al., "Development of a T1 Contrast Agent for Magnetic Resonance Imaging Using MnO Nanoparticles," Angew. Chem., Int. Ed. (2007), 46, 5397-5401. (Published online Mar. 13, 2007).

Slowing et al., "Mesoporous Silica Nanoparticles for Intracellular Delivery of Membrane-Impermeable Proteins," J. Am. Chem. Soc. (2007), 129, 8845-8849. (Published online Jun. 23, 2007).

Huang et al., "Cancer Cell Imaging and Photothermal Therapy in the Near-Infrared Region by Using Gold Nanorods" J. Am. Chem. Soc. (2006), 128, 2115-2120. (Published online Jan. 21, 2006).

Chen et al., "Immuno Gold Nanocages with Tailored Optical Properties for Targeted Photothermal Destruction of Cancer Cells," Nano Lett. (2007); 7, 1318-1322. (Published online Apr. 15, 2007).

Gobin et al., "Near-Infrared Resonant Nanoshells for Combined Optical Imaging and Photothermal Cancer Therapy," Nano Lett. (2007), 7, 1929-1934. (Published online Jun. 6, 2007).

Kohler et al., "Methotrexate-Immobilized Poly(ethylene glycol) Magnetic Nanoparticles for MR Imaging and Drug Delivery," Small (2006), 2, 785-792.

Medarova et al., "In Vivo Imaging of siRNA Delivery and Silencing in Tumors," Nat. Med. (2007), 13, 372-377. (Published online Feb. 25, 2007).

Jana et al., "Size- and Shape-Controlled Magnetic (Cr, Mn, Fe, Co, Ni) Oxide Nanocrystals via a Simple and General Approach," Chem. Mater. (2004), 16, 3931-3935.

Park, et al., "Ultra-Large-Scale Syntheses of Monodisperse Nanocrystals," Nat. Mater. (2004), 3, 891-895.

Sun et al., "Monodisperse $MFe_2O^4$ (M = Fe, Co, Mn) Nanoparticles," J. Am. Chem. Soc. (2004), 126, 273-279.

Yu et al., "Synthesis of Monodisperse Iron Oxide Nanocrystals by Thermal Decomposition of Iron Carboxylate Salts," Chem. Commun. (2004), 2306-2307.

Jun et al., "Nanoscale Size Effect of Magnetic Nanocrystals and Their Utilization for Cancer Diagnosis via Magnetic Resonance Imaging," J. Am. Chem. Soc. (2005), 127, 5732-5733.

Fan et al., "Self-Assembly of Ordered, Robust, Three-Dimensional Gold Nanocrystal/Silica Arrays," Science (2004), 304, 567-571.

Fan et al., "Ordered Nanocrystal/Silica Particles Self-Assembled from Nanocrystal Micelles and Silicate," Chem. Commun. (2006), 2323-2325. (Published online Mar. 29, 2006).

Kim et al., "Magnetic Fluorescent Delivery Vehicle Using Uniform Mesoporous Silica Spheres Embedded with Monodisperse Magnetic and Semiconductor Nanocrystals," J. Am. Chem. Soc. (2006), 128, 688-689. (Published onlineDec. 31, 2005).

Jiang et al., "Aerosol-Assisted Self-Assembly of Single-Crystal Core/Nanoporous Shell Particles as Model Controlled Release Capsules," J. Am. Chem. Soc. (2006), 128, 4512-4513. (Published online Mar. 16, 2006).

Lee et al., "Dual-Mode Nanoparticle Probes for High-Performance Magnetic Resonance and Fluorescence Imaging of Neuroblastoma," Angew. Chem., Int. Ed. (2006), 118, 8340-8342. (Published online Nov. 14, 2006).

Lin et al., "Multifunctional Composite Nanoparticles: Magnetic, Luminescent, and Mesoporous," Chem. Mater. (2006), 18, 5170-5172. (Published online Oct. 10, 2006).

Wang et al., "Fluorescent Nanoparticles for Multiplexed Bacteria Monitoring," Bioconjugate Chem. (2007), 18, 297-301. (Published online Mar. 7, 2007).

Cai et al., "Dilute Solution Routes to Various Controllable Morphologies of MCM-41 Silica with a Basic Medium," Chem. Mater. (2001), 13, 258-263.

Lin et al., "Well-Ordered Mesoporous Silica Nanoparticles as Cell Markers," Chem. Mater. (2005), 17, 4570-4573.

Brust et al., "Synthesis of Thiol-Derivatised Gold Nanoparticles in a Two-Phase Liquid-Liquid System," Chem. Commun. (1994), 801-802.

Hiramatsu et al., "A Simple Large-Scale Synthesis of Nearly Monodisperse Gold and Silver Nanoparticles with Adjustable Sizes and with Exchangeable Surfactants," Chem. Mater. (2004), 16, 2509-2511.

Slowing et al., "Effect of Surface Functionalization of MCM-41-Type Mesoporous Silica Nanoparticles on the Endocytosis by Human Cancer Cells," J. Am. Chem. Soc. (2006), 128, 14792-14793. Published online Nov. 2, 2006).

Lu et al., "Mesoporous Silica Nanoparticles as a Delivery System for Hydrophobic Anticancer Drugs," Small (2007), 3, 1341-1346. (Published online Jun. 13, 2007).

Yi et al., "Nanoparticle Architectures Templated by $SiO_2$-$Fe_2O_3$ Nanocomposites," Chem. Mater. (2006), 18, 614-619.

Lang et al., "A Fast and Efficient Ion-Exchange Procedure to Remove Surfactant Molecules from MCM-41 Materials," Chem. Mater. (2004), 16, 1961-1966.

Grün et al., The Synthesis of Micrometer- and Submicrometer-Size Spheres of Ordered Mesoporous Oxide MCM-41, Adv. Mater. (1997), 9, 254-257.

Xu et al., "Room-Temperature Preparation and Characterization of Poly(ethylene glycol)-Coated Silica Nanoparticles for Biomedical Applications," J. Biomed. Mater. Res., Part A (2003), 66A, 870-879.

Zhang et al., "Synthesis of Poly(ethylene glycol) (PEG)-Grafted Colloidal Silica Particles with Improved Stability in Aqueous Solvents," J. Colloid Interface Sci. (2007), 310, 446-455 (Feb. 14, 2007).

Gerion et all, "Synthesis and Properties of Biocompatible Water-Soluble Silica-Coated CdSe/ZnS Semiconductor Quantum Dots," J. Phys. Chem. B (2001), 105, 8861-8871.

Bagwe et al., "Surface Modification of Silica Nanoparticles to Reduce Aggregation and Nonspecific Binding," Langmuir (2006), 22, 4357-4362 (Apr. 25, 2006).

Corot et al., "Recent Advances in Iron Oxide Nanocrystal Technology for Medical Imaging," Adv. Drug Delivery Rev. (2006), 58, 1471-1504.

Sudimack et al., "Targeted Drug Delivery Via the Folate Receptor," Adv. Drug Delivery Rev. (2000), 41, 147-162.

(56) References Cited

OTHER PUBLICATIONS

Kam et al., "Carbon Nanotubes as Multifunctional Biological Transporters and Near-Infrared Agents for Selective Cancer Cell Destruction," *Proc. Natl. Acad. Sci. USA* (2005), 102, 11600-11605.
Mal et al., "Photo-Switched Storage and Release of Guest Molecules in the Pore Void of Coumarin-Modified MCM-41," *Chem. Mater.* (2003), 15, 3385-3394.
Nguyen et al., "Design and Optimization of Molecular Nanovalves Based on Redox-Switchable Bistable Rotaxanes," *J. Am. Chem. Soc.* (2007), 129, 626-634. (Published online Jan. 3, 2007).
Zhu et al., "Installing Dynamic Molecular Photomechanics in Mesopores: A Multifunctional Controlled-Release Nanosystem," *Angew. Chem., Int. Ed.* (2007), 46, 2241-2244.
Lee et al., "Delivery of Liposomes into Cultured KB Cells via Folate Receptor-Mediated Endocytosis," *J. Biol. Chem.* (1994), 269, 3198-3204. (Publ.
Soppimath et al., "Multifunctional Core/Shell Nanoparticles Self-Assembled from pH-Induced Thermosensitive Polymers for Targeted Intracellular Anticancer Drug Delivery," *Adv. Funct. Mater.* (2007), 17, 355-362. (Published online Jan. 9, 2007).
Muggia et al., *Ann. N. Y. Acad. Sci.* (1996), 803, 213.
Litvak et al., *Surgery* (1999), 126, 223.
Abigerges et al., *Clin. Oncol.* (1995), 13, 210.
Keane et al., *J. Urol.* (1998), 160, 252.
Miller et al., *Invest. New Drugs* (2004), 22, 69.
Masuda et al., J. Clin. Oncol. (1992), 10, 1225.
Hertzberg et al., J. Med. Chem. (1989), 32, 715.
Scott et al., Pharm. Res. 1993, 10, 1451.
Onishi et al., Curr. Drug Discovery Technol. (2005), 2, 169.
Fuchs et al., Cancer Treat. Rev. (2006), 32, 491.
Cunha et al., Mutagenesis (2002), 17, 141.
Kresge, et al., Nature (1992), 359, 0028.
Munoz, et al., Chem. Mater. (2003), 15, 500.
Han et al., J. Am. Chem. Soc. (1999), 121, 9897.
Stein et al., Adv. Mater. (2000), 12, 1403.
Arruebo et al., Chem. Mater. (2006), 18, 1911. (Published online Mar. 14, 2006).
Arruebo et al., Nanotechnology (2006), 17, 4057 (Published Jul. 18, 2006).
Radu et al., J. Am. Chem. Soc. (2004), 126, 13216.
Lin et al., Chem. Mater. (2005), 17, 4570.
Lai et al., J. Am. Chem. Soc. (2003), 125, 4451.
Huh et al., Chem. Mater. (2003), 15, 4247.
Canonico et al., J. Cell Biol. (1969), 43, 367.
Hasegawa et al., Cancer Res. (1996), 56, 1713.
Wagner et al., Nat. Biotechnol. (Oct. 2006), 24, 1211.
Chen et al., *J. Biol. Chem.*, (1988), 263, 8754-8758.
Lu et al., *Small*, (2007), 3, 1341-1346. (Published online Jun. 13, 2007).
Lichstein et al., *J. Bacteriol.* (1944), 47, 231-238.
Heuser et al., *J. Cell Biol.* (1989), 108, 389-400.
Wessing et al., *J. Comp. Physiol.* (1993), 163, 452.
Pearse et al., *Annu. Rev. Biophys. Biophys. Chem.* (1987), 16, 49-68.
Harvey et al., *Amer. Zool.* (1998), 38, 426-441.
Samson et al., *J. Pharmacol. Exp. Ther.* (1979), 208, 411-417.
Roma et al. *Hepatology*, (2000), 32, 1342-1356.
Chung et al., *Biomaterials*, (2007), 28, 2959-2966 (Published online Mar. 19, 2007).
Kim et al., J. Vet. Sci. (2006), 7, 321-326.
Gemeinhart et al., Biotechnol. Prog. (2005), 21, 532-537.
Xing et al., J. Nanosci. Nanotechnol. (2005), 5, 1688-1693.
Wani et al., J. Am. Chem. Soc. (1971), 93, 2325-2327.
Luo et al., Nat. Biotechnol. (2000), 18, 893-895.
Jin et al., Chem Res Toxicol (2007). (Published online Jul. 13, 2007).
Zhu, et al., Installing Dynamic Molecular Photomechanics in Mesopores: A Multifunctional Controlled-Release Nanosystem, Angew. Chem. Int. E. 2007, 46, 2241-2244. (Published online Feb. 13, 2007).

Shaobin Wang, Microporous and Mesoporous Materials, Department of Chemical Engineering, 117, (2009), pp. 1-9. (Published online, Jul. 9, 2008).
Irene Brigger. et al., Nanoparticles in cancer therapy and diagnosis, Advanced Drug Delivery Reviews (2002), pp. 631-651.
Si-Han Wu, et al. Multifunctional Mesoporous Silica Nanoparticles for Intracellular Labeling and Animal Magnetic Resonance Imaging Studies, ChemBioChem., (2008) 9, pp. 53-57. (Published online Nov. 12, 2007).
Mark E. Davis, et al., Nanoparticle therapeutics: an emerging treatment modality for cancer, Nature Reviews, vol. 7, Sep. 2008, pp. 771-782.
Pankaj V. Paranjpe, et al., Tumor-targeted bioconjugate based deliver of camptothecin: design, synthesis and in vitro evaluation, Journal of Controlled Release, 100 (2004), pp. 275-292.
Luigi Pasqua, et al., Preparation of bifunctional hybrid mesoporous silica potentially useful for drug targeting, Microporous and Mesporous Materials 103 (2007), pp. 166-173. (Published online Feb. 3, 2007).
Chih-Pin Tsai, et al. High-Contrast Paramagnetic Fluorescent Mesoporous Silica Nanrods as a Multifunctional Cell-Imaging Probe, Small 2008, 4, No. 2, pp. 186-191. (Published online Jan. 18, 2008.
Swadeshmukul Santra, Folate Conjugated Fluorescent Silica Nanoparticles for Labeling Neoplastic Cells, Nanotech, (2005), vol. 5, No. 6, pp. 899-904.
Lu et al., "Mesoporous Silica Nanoparticles for Cancer Therapy: Energy-Dependent Cellular Uptake and Delivery of Paclitaxel to Cancer Cells", 2007, Nanobiotechnology, vol. 3, pp. 89-95.
Tamanoi (2006) Nanodelivery: Towards controlled release of anticancer drugs. Oral Presentation on Dec. 6, 2006 (see NanoBio-Tokyo 2006 Program), 7pages. Abstract provided in *Proceedings of UT Symposium on NanoBio Integration Program* and Abstract provided.
Stöber et al. (1968) "Controlled growth of monodisperse silica spheres in the micron size range" *J. Colloid and Interface Sci.*, 26: 62-69.
Angelos et al., (2007) "Photo-Driven Expulsion of Molecules from Mesostructured Silica Nanoparticles," *J Phys Chem C*, 111:6589-6592.
Nguyen et al., (2007) "Versatile Supramolecular Nanovalves Reconfigured for Light Activation" *Adv. Funct. Mater.*, 17:2101-2110.
Leung et al., (2006) "Supramolecular Nanovalves Controlled by Proton Abstraction and Competitive Binding" *Chem. Mater.*, 18:5919-5928.
Nguyen et al., (2005) "A reversible molecular valve," *Proc. Natl. Acad. Sci. USA.*, 102:10029-10034.
U.S. Office Action, dated Jul. 10, 2012, issued in U.S. Appl. No. 12/812,359.
U.S. Office Action, dated Feb. 14, 2013, issued in U.S. Appl. No. 12/812,359.
U.S. Final Office Action, dated Jul. 26, 2013, issued in U.S. Appl. No. 12/812,359.
U.S. Final Office Action (Letter Restarting Period for Response), dated Jul. 29, 2013, issued in U.S. Appl. No. 12/812,359.
U.S. Office Action (Before the Patent Trial and Appeal Board, Examiner's Answer to Appeal Brief), dated Aug. 28, 2014, issued in U.S. Appl. No. 12/812,359.
U.S. Office Action (Restriction Requirement), dated May 21, 2012, issued in U.S. Appl. No. 12/841,331.
U.S. Office Action, dated Aug. 13, 2012, issued in U.S. Appl. No. 12/841,331.
U.S. Office Action, dated Apr. 30, 2013, issued in U.S. Appl. No. 12/841,331.
U.S. Final Office Action, dated Dec. 26, 2013, issued in U.S. Appl. No. 12/841,331.
U.S. Office Action, dated Dec. 10, 2014, issued in U.S. Appl. No. 12/841,331.
U.S. Final Office Action, dated May 13, 2015, issued in U.S. Appl. No. 12/841,331.
U.S. Office Action, dated Jan. 20, 2016, issued in U.S. Appl. No. 12/841,331.

(56) References Cited

OTHER PUBLICATIONS

U.S. Office Action (Restriction Requirement), dated Nov. 26, 2012, issued in U.S. Appl. No. 13/140,714.
U.S. Office Action, dated May 10, 2013, issued in U.S. Appl. No. 13/140,714.
U.S. Final Office Action, dated Feb. 28, 2014, issued in U.S. Appl. No. 13/140,714.
U.S. Office Action, dated Mar. 13, 2015, issued in U.S. Appl. No. 13/140,714.
U.S. Final Office Action, dated Nov. 20, 2015, issued in U.S. Appl. No. 13/140,714.
U.S. Office Action (Restriction Requirement), dated Jul. 7, 2015, issued in U.S. Appl. No. 13/550,374.
U.S. Office Action, dated Dec. 16, 2015, issued in U.S. Appl. No. 13/550,374.
U.S. Office Action (Restriction Requirement), dated Mar. 29, 2013, issued in U.S. Appl. No. 13/428,830.
U.S. Office Action, dated Oct. 3, 2013, issued in U.S. Appl. No. 13/428,830.
U.S. Final Office Action, dated Aug. 1, 2014, issued in U.S. Appl. No. 13/428,830.
U.S. Office Action, dated Dec. 5, 2014, issued in U.S. Appl. No. 13/428,830.
U.S. Final Office Action, dated Jul. 23, 2015, issued in U.S. Appl. No. 13/428,830.
U.S. Office Action, dated May 16, 2016, issued in U.S. Appl. No. 13/428,830.
PCT International Preliminary Report on Patentability and Written Opinion dated Jun. 8, 2010 issued in PCT/US08/13476.
PCT International Search Report and Written Opinion dated May 19, 2009 issued in PCT/US09/031872.
PCT International Preliminary Report on Patentability dated Aug. 5, 2010 issued in PCT/US09/031872.
PCT International Search Report and Written Opinion dated Mar. 27, 2009 issued in PCT/US2009/032451.
PCT International Preliminary Report on Patentability and Written Opinion dated Aug. 12, 2010 issued in PCT/US2009/032451.
PCT International Search Report and Written Opinion dated May 28, 2009 issued in PCT/US2009/031891.
PCT International Preliminary Report on Patentability and Written Opinion dated Aug. 5, 2010 issued in PCT/US2009/031891.
PCT International Search Report dated Sep. 3, 2010 issued in PCT/US2009/068816.
PCT International Preliminary Report on Patentability and Written Opinion dated Jun. 30, 2011 issued in PCT/US2009/068816.
PCT International Search Report dated Apr. 6, 2012 issued in PCT/US2011/043874.
PCT International Preliminary Report on Patentability dated Jan. 24, 2013 issued in PCT/US2011/043874.
PCT International Search Report and Written Opinion dated Jun. 24, 2014 issued in PCT/US2014/020857.
PCT International Report on Patentability and Written Opinion dated Sep. 17, 2015 issued in PCT/US2014/020857.
Alvaro et al., (2005) *Chem. Mater.*,17:4958-4964.
Angelos et al., (2007) "Mesostructured silica supports for functional materials and molecular machines," *Adv. Funct. Mater.*, 17:2261-2271.
Aprahamian et al., (2007) *Org. Lett.*, 9:1287.
Arnold et al., (2004) "Activation of Integrin Function by Nanopatterned Adhesive Interfaces," *ChemPhysChem*, 5:383-388.
Arola et al., (2000) *Cancer Res.*, 60:1789-1792.
Barbe et al., (2004) "Silica particles: A novel drug-delivery system," *Adv. Mater.*, 16:1959-1966.
Beck et al., (1992) "A new family of mesoporous molecular sieves prepared with liquid crystal templates," *J. Am. Chem. Soc.*, 114:10834-10843.
Belloc et al., (1994) *Cytometry*, 17:59.
Berry et al., (2005) "Self-Assembly of nanoparticles on live bacterium: An avenue to Fabricate Electronic Devices," *Angew. Chem., Int. Ed.*, 44:6668-6673.

Besson et al., (2005) *J. Mater. Chem.*, 15:803-809.
Bettio et al., (2006) *J. Nucl. Med.*,1153-1160.
Bharali et al., (2005) *Proc. Natl. Acad. Sci. USA.*, 102:11539-11544.
Blow et al., (2007) *Nature*, 450:1117-1120.
Borm et al., (2006) *Toxicol. Sci.*, 90:23-32.
Botella et al., (2007) "Single gold nanoparticles encapsulated in monodispersed regular spheres of mesostructured silica produced by pseudomorphic transformation," *Chem. Mater*, 19:1979-1983.
Boussif et al., (1995) *Proc. Natl. Acad. Sci. U.S.A.*, 92:7297-7301.
Braunschweig et al., (2007) *Chem. Asian J.*, 2:634.
Butler et al., (2006) "Purified Integrin Adhesion Complexes Exhibit Actin-Polymerization Activity," *Curr. Biol.*, 16:242-251.
California Nano Systems Institute 2005 Annual Research Report: "Powered Artificial Nano-Machines: Molecular Valves and Impellers," URL:http://www.cnsi.ucla.edu/spheres/ResReport-2005.pdf [retrieved on Jul. 8, 2010], p. 51.
Cavalcanti-Adam et al., (2007) "Cell Spreading and Focal Adhesion Dynamics are Regulated by Spacing of Integrin Ligands," *Biophys. J.*, 92:2964-2974.
Celano et al., (2004) "Cytotoxic effects of Gemcitabine-loaded liposomes in human anaplastic thyroid carcinoma cells," BMC Cancer, 4(63):5 pages.
Champion et al., (2006) "Role of Target Geometry in Phagocytosis," *Proc. Natl. Acad. Sci. U.S.A.*, 103:4930-4934.
Champion et al., (2007) "Making Polymeric Micro- and Nanoparticles of Complex Shapes," *Proc. Natl. Acad. Sci. U.S.A.*, 104:11901-11904.
Champion et al., (2007) "Particle shape: A New Design Parameter for Micro- and Nanoscale Drug Delivery Carriers," *J. Control. Release*, 121:3-9.
Chen et al., (1996) "Requirement of CDC42 for Salmonella-Induced Cytoskeletal and Nuclear Responses," *Science*, 274:2115-2118.
Chithrani et al., (2006) "Determining the Size and Shape Dependence of Gold Nanoparticle Uptake into Mammalian Cells," *Nano Lett.*, 6:662-668.
Chithrani et al., (2007) "Elucidating the Mechanism of Cellular Uptake and Removal of Protein-Coated Gold Nanoparticles of Different Sizes and Shapes," *Nano Lett.*, 7:1542-1550.
Clottens et al., (1997) *Occup. Environ. Med.*, 54:376-387.
Conner et al., (2003) "Regulated Portals of Entry into the Cell," *Nature*, 422:37-44.
Darbre et al., (2006) *Chem. Res.*, 39:925.
Darzynkiewicz et al., (1997) *Cytometry*, 27:1.
De Smedt et al., *Pharmaceutical Research*, 17(2):113-126.
de Wolf et al., (2007) *Int. J. Pharm.*, 331:167-175.
Denny et al., (2004) *Cancer Invest.*, 22:604.
Derfus et al., (2007) *Adv. Mater.*, 19:3932-3936.
Dhanikula et al., (2006) *Chem.*, 17:29.
Dharmawardhane et al., (2000) "Regulation of Macropinocytosis by p21-activated Kinase-1," *Mol. Biol. Cell*, 11:3341-3352.
Dichtel et al., (2006) *J. Am. Chem. Soc.*, 128:10388.
Discher et al., (2005) "Tissue Cells Feel and Respond to the Stiffness of Their Substrate," *Science*, 310:1139-1143.
Duan et al., (2007) *J Am. Chem. Soc.*, 129:3333-3338.
Duncan et al., (2005) *Endocr-Relat. Cancer.*, 12:S189-S199.
Duncan et al., (2006) *J. Drug Target.*,14:337-341.
Fang et al., (2004) "Factors and Mechanism of "EPR" Effect and the Enhanced Antitumor Effects of Macromolecular Drugs Including SMANCS," In *Polymer Drugs in the Clinical Stage*, Springer US, 519:29-49.
Faris et al., (1991) *Clin. Phys. Phgsiol. Meas.*, 12:353-358.
Fenske et al., (2001) *Curr. Opin. Mol. Ther.*, 3:153-158.
Ferrari et al., (2005) *Nat. Rev. Cancer*, 5:161-171.
Fiorentini et al., (2001) "Activation of Rho GTPases by Cytotoxic Necrotizing Factor 1 Induces Macropinocytosis and Scavenging Activity in Epithelial Cells," *Mol. Biol. Cell*, 12:2061-2073.
Florea et al., (2002) *AAPS PharmSci.*, 4:E12.
Frangioni et al., (2003) "In vivo near-infrared fluorescence imaging," *Curr. Opin. Chem*, 7:626-634.
Frisch et al., (1996) "Nanocomposites Prepared by Threading Polymer Chains through Zeolites, Mesoporous Silica, or Silica Nanotubes," *Chem. Mater.*, 8(8):1735-1738.

(56) References Cited

OTHER PUBLICATIONS

Gamen et al., (2000) "Doxorubicin Treatment Activates a Z-VAD-Sensivitve Caspase, Which Causes $\Delta\Psi_m$ Loss, Caspase-9 Activity, and Apoptosis in Jurkat Cells," *Exp. Cell Res.*, 258:223-235.
Garg et al., (2002) "Editorial: Hepatic Steatosis, Insulin Resistance, and Adipose Tissue Disorders," *J. Clin. Endocrinol. Metab.*, 87:3019-3022.
Giri et al., (2005) *Angew. Chem. Int. Ed.*,44:5038-5044.
Glass et al., (2003) "Micro-Nanostructured Interfaces Fabricated by the Use of Inorganic Block Copolymer Micellar Monolayers as Negative Resist for Electron-Beam Lithography," *Adv. Funct. Mater.*, 13:569-575.
Glass et al., (2004) "Block Copolymer Micelle Nanolithography on Non-Conductive Substrates," *New J. of Phys.*, 6:101.
Godbey et al., (1999) *Proc. Natl. Acad. Sci. U.S.A.*, 96:5177-5181.
Gopin et al., (2006) *Bioconjug. Chem*, 17:1432-1440.
Gottesman et al., (2002) *Annu. Rev. Med.*, 53:614-627.
Harada, (2001) "Cyclodextrin-Based Molecular Machines," *Accounts of Chemical Research*, 34:456-464.
Hayek et al., (2005) *N. Engl. J. Med.*, 352:2456-2457.
Hernandez et al., (2001) *J. Am. Chem. Soc.*, 123:1248-1249.
Hernandez et al., (2004) *Am. Chem. Soc.*, 126:3370-3371.
Hirano et al., (1979) *Makromol. Chem.*, 180:1125-1131.
Ho et al., (2004) "Nanoseparated polymeric networks with multiple antimicrobial properties," *Adv. Mater*, 16(12):957-961.
Hoet et al., (1999) *Toxicol. Sci.*, 52:209-216.
Hoet et al., (2001) *Toxicol. Appl. Pharmacol.*, 175:184-190.
Huang et al., (1998) *Langmuir*, 14:7331.
Hughes (2005) "Nanostructure-mediated drug delivery," *Nanomedicine: Nanotechnology, Biology, and Medicine*, 1:22-30.
Iyer et al., (2006) Drug Discov. Today, 11:812-818.
Jabr-Milane et al., (2008) *Cancer Treat. Rev.*, 34:592-602.
Jana et al., (2007) "Synthesis of Water-Soluble and Functionalized Nanoparticles by Silica Coating," *Chem Mater*, 19:5074-5082.
Lu et al., (2007) *Small*, 3:1341-1346.
Judge et al., (2006) *Mol. Ther.*, 13:494-505.
Kataoka et al., (2001) *Adv. Drug Delivery Rev.*, 47:113-131.
Kaul et al., (2004) *J. Drug Target.*, 12:585-591.
Kawano et al., (2006) *J. Controlled Release*, 111:382-389.
Kim (2002) "Mechanically interlocked molecules incorporating cucurbituril and their supramolecular assemblies," *Chem. Soc. Rev.*, 32:96-107.
Kircheis et al., (1999) *J. Gene. Med.*, 1:111-120.
Kircheis et al., (2002) *Cancer Gene. Ther.*, 9:673-680.
Kneuer et al., (2000) *Bioconjugate Chem.*, 11:926-932.
Kocer et al., (2005) *Science*, 309:755.
Kónya et al., (2003) "Synthetic Insertion of Gold Nanoparticles into Mesoporous Silica," Chem Mater, 15(6):1242-1248.
Kremer et al., (1996) "Computer Visualization of Three-dimensional Image Data Using IMO," *J. Struct. Biol*, 116:71-76.
Kunath et al., (2002) *Pharm. Res.*, 19:810-817.
Kursa et al., (2003) *Bioconjugate Chem.*, 14:222-231.
Lee et al., (2005) *Nat. Biotechnol.*, 23:1517.
Li et al., (1999) "Preparation of $Ag/SiO_2$ nanosize composites by a reverse micelle and sol-gel technique," *Langmuir*, 15:4328-4334.
Li et al., (2003) "Facilitation of $Ca^{2+}$-Dependent Exocytosis by Rac1-GTPase in Bovine Chromaffin," *Cells. J. Physiol.*, 550:431-445.
Lim et al., (1997) *J. Am. Chem. Soc.*, 119:4090-4091.
Liu et al., (2002) "Self-Directed Assembly of Photoactive Hybrid Silicates Derived from an Azobenzene-Bridged Silsesquioxane," *J. Am. Chem. Soc.*, 124:14540-14541.
Liu et al., (2003) *Angew. Chem. Int. Ed., Engl.*, 42:1731-1734.
Liu et al., (2003) *Chem. Comm.*, 10:1144-1145.
Liu et al., (2004) *J. Nano Lett.*, 4:551-554.
Lobo et al., (2007) "Paclitaxel Albumin-Bound Particles (Abraxane(TM)) in Combination with Bevacizumab with or without Gemcitabine: Early Experience at the University of Miami/Braman Family Breast Cancer Institute," *Biomed. Pharmacother.*, 61:531-533.
Lok et al., (2006) "Proteomic analysis of the mode of antibacterial action of silver nanoparticles," *Journal of Proteome Research*, 5:916-924.
Lu et al., (1997) *Nature*, 389:364-368.
Lu et al., (2002) "Modifying the surface properties of superparamagnetic iron oxide nanoparticles through a sol-yel approach," *Nano Letter*, 2(3):183-186.
Ludwig et al., (2006) *Cancer Res.*, 66:4808-4815.
Mal et al., (2003) *Nature*, 421:350-353.
Mao et al., (2005) *Pharm. Res.*, 22:2058-2068.
McBain et al., (2007) *J. Mater. Chem.*, 17:2561-2565.
Mignot et al., (2001) "Distribution of s-layers on the surface of bacillus cereus strains: phylogenetic origin and ecological pressure," *Environ. Microbiol.*, 3(8):493-501.
Miljanic et al., (2006) *Org. Lett.*, 8:4835.
Minko et al., (2000) *Pharm. Res.*, 17:505-517.
Minoofar et al., (2002) "Placement and characterization of pairs of luminescent molecules in spatially separated regions of nanostructured thin films," *J. Am Chem. Soc.*, 124:14388-14396.
Minoofar et al., (2005) "Multiply doped nanostructured silicate sol-gel thin films: Spatial segregation of dopants, energy transfer, and distance measurements," *J. Am. Chem. Soc.*, 127:2656-2665.
Moller et al., (2007) "Colloidal Suspensions of Nanometer-Sized Mesoporous Silica," *Adv. Funct. Mater.*, 17:605-612.
Mulvaney, (1996) "Surface Plasmon Spectroscopy of Nanosized Metal Particles," *Langmuir*, 12:788-800.
Nakamura et al., (2007) "Direct synthesis of monodispersed thiol-functionalized nanoporous silica spheres and their application to a colloidal crystal embedded with gold nanoparticles," *J Mater Chem*, 17:3726-3732.
Nakase et al., (2004) "Cellular Uptake of Arginine-Rich Peptides: Roles for Macropinocytosis and Actin Rearrangement," *Mol. Ther.*, 10:1011-1022.
Neu et al., (2005) *J. Gene. Med.*, 7:992-1009.
Nguyen et al., (2006) "Construction of a pH-Driven Supramolecular Nanovalve," *Organic Letters*, 8(15):3363-3366.
Nie et al., (2007) *Annu. Rev. Biomed. Eng.*, 9:12.1-12.32.
Noguchi et al., (1998) *Cancer Sci.*, 89:307-314.
Nomura et al., (2007) *Am. J. Roentgenol.*, 189:1484-1488.
Ohsuna et al., (2005) "Characterization of Chiral Mesoporous Materials by Transmission Electron Microscopy," *Small*, 1:233-237.
Osada et al., (1999) "Effect of Mechanical Strain on Gastric Cellular Migration and Proliferation During Mucosal Healing: Role of Rho Dependent and Rac Dependent Cytoskeletal Reorganisation," *Gut*, 45:508-515.
Paciotti et al., (2006) "Colloidal Gold Nanoparticles: A Novel Nanoparticle Platform for Developing Multifunctional Tumor-Targeted Drug Delivery Vectors," *Drug Dev Res*, 67:47-54.
Padilla De Jesus et al., (2002) *Bioconjug Chem.*, 13:453-461.
Pal et al., (2007) "Does the Antibacterial Activity of Silver Nanoparticles Depend on the Shape of the Nanoparticle? A Study of the Gram-Negative Bacterium *Escherichia coli,*" *Applied and Environmental Microbiology*, 73 (6): 1712-1720.
Pantos et al., (2005) *Langmuir*, 21:7483-7490.
Park et al., (2007) "Controlled Release of Guest Molecules from Mesoporous Silica Particles Based on a pH-Responsive Polypseudorotaxane Motif" *Angew. Chem. Int. Ed.*, 46:1455-1457 [ABSTRACT provided].
Petersen et al., (2002) *Bioconjugate Chem.*, 13:845-854.
Portney et al., (2006) *Anal. Bioanal. Chem.*, 386:620-630.
Radu et al., (2004) "A Polyamidoamine Dendrimer-Capped Mesoporous Silica Nanosphere-Based Gene Transfection Reagent," *J. Am. Chem. Soc.*, 126:13216-13217 [and supporting information attached].
Radu et al., (2004) *J. Am. Chem. Soc.*, 126:13216-13217.
Ridley et al., (1992) "The Small GTP-binding Protein Rae Regulates Growth Factor-Induced Membrane Ruffling," *Cell*, 70:401-410.
Rostovtsev et al., (2002) *Angew. Chem., Int. Ed.*, 41:2596-2599.
Saha et al., (2005) *Chem. Euro. J.*, 11:6846-6858.
Santra et al., (2004) *Chem. Commun.*, 2810-2811.
Schiestel et al., (2004) "Controlled Surface Functionalization of Silica Nanospheres by Covalent Conjugation Reactions and Prepa-

(56) References Cited

OTHER PUBLICATIONS ration of High Density Streptavidin Nanoparticles," *Journal of Nanoscience and Nanotechnology*,4(5):504-511.
Schrijvers et al., (2004) "Flow Cytometric Evaluation of a Model for Phagocytosis of Cells Undergoing Apoptosis," *J. Immunol. Methods*, 287:101-108.
Shrivastava et al., (2007) "Characterization of enhanced antibacterial effects of novel silver nanoparticles," *Nanotechnology*, 18:225103(9pp).
Sierocki et al., (2006) *J. Phys. Chem. B*, 110:24390-24398.
Slowing et al., (2007) *Adv. Funct. Mater.*, 17:1225-1236.
Sonawane et al., (2002) *J. Biol. Chem.*, 277:5506-5513.
Sondi et al., (2004) "Silver nanoparticles as antimicrobial agent: a case study on *E. coli* as a model for Gram-negative bacteria," *Journal of Colloid and Interface Science*, 275:177-182.
Suzuki et al., (1981) *J. Natl. Cancer Inst.*, 67:663-669.
Szakacs et al., (2006) *Nat. Rev. Drug Discov.*, 5:219-234.
Tang et al., (2003) *Biomaterials*, 24:2351-2362.
Tarimala et al., (2006) "New Appraoch to antibacterial treatment of cotton fabrc with silver nanoparticle-doped silica using sol-gel process," *J. Appl. Poly. Sci.*, 101:2938-2943.
Thery et al., (2006) "Anisotropy of Cell Adhesive Microenvironment Governs Cell Internal Organization and Orientation of Polarity," *Proc. Natl. Acad. Sci. U.S.A.*, 103:19771-19776.
Thiel et al., (2007) "Antibacterial Properties of Silver-Doped Titania," *Small*, 3(5):799-803.
Tietze et al., (2006) *Angew. Chem. Int. Ed.*, 45:6574.
Torney et al., (2007) *Nat. Nanotechnol.*, 2:295-300.
Tornoe et al., (2002) *J. Org. Chem.*, 67:3057.
Trewyn et al., (2004) "Morphological Control of Room-Temperature Ionic Liquid Templated Mesoporous Silica Nanoparticles for Controlled Release of Antibacterial Agents," *Nano Letter*, 4(11):2139-2143.
Ung et al., (1998) "Controlled Method for Silica Coating of Silver Colloids. Influence of Coating on the Rate of Chemical Reactions," *Langmuir*, 14:3740-3748.
Urban-Klein et al., (2005) *Gene Ther.*, 12:461-466.
Vallet-Regi et al., (2001) *Chem. Mater.*, 13:308-311.
Vallet-Regi et al., (2007) "Mesoporous Materials for Drug Delivery," *Angew. Chem., Int. Ed.*, 46:7548-7558.
van Vlerken et al., (2007) *Cancer Res.*, 67:4843-4850.
Verbaan et al., (2004) *J. Gene Med.*, 6: 64-75.
Wang et al., (2007) "Fluorescent Nanoparticles for Multiplexed Bacteria Monitoring," *Bioconjugate Chem.*, 18:297-301 (Published online Mar. 7, 2007).
Weh et al., (2002) *J. Microporous Mesoporous Mater.*, 54:15-26.
West et al., (1989) "Distinct Endocytotic Pathways in Epidermal Growth Factor-Stimulated Human Carcinoma A431 Cells," *J. Cell Biol.*, 109:2731-2739.
Woodroofe et al., (2003) *J. Am. Chem. Soc.*, 125:11458.
Word Counts of Abstract (AN12/841331), one page.
Wu et al., (2007) *J Pharm. Pharmaceut. Sci.*, 10:350-357.
Xia et al., (2006) *Nano Lett.*, 6:1794-1807.
Yager et al., (2006) "Novel photo-switching using azobenzene functional materials," *Journal of Photochemistry and Photobiology, A: Chemistry*, 182:250-261.
Yagmurca et al., (2004) *Clinica. Chimica. Acta.*, 348:27-34.
Yang et al., (2006) "On the Origin of Helical Mesostructures," *J. Am. Chem. Soc.*, 128:10460-10466.
Yang et al., (2007) "Siliceous Nanopods from a Compromised Dual-Templating Approach," *Angew. Chem. Int. Ed. Engl.*, 46:8579-8582.

Ying et al., (1999) "Synthesis and Applications of Supramolecular-Templated Mesoporous Materials," *Angew. Chem., Int. Ed*, 38:56-77.
Zhao et al., (2004) "In situ formation of silver nanoparticles inside pore channels of ordered mesoporous silica," *Mater. Lett.*, 58:2152-2156.
Zhu et al., (2004) *Biotechnol. Appl. Biochem.*, 39:179-187.
U.S. Office Action (Before the Patent Trial and Appeal Board, Decision on Appeal), dated Aug. 31, 2016, issued in U.S. Appl. No. 12/812,359.
U.S. Final Office Action, dated Aug. 18, 2016, issued in U.S. Appl. No. 12/841,331.
U.S. Office Action, dated Dec. 2, 2016, issued in U.S. Appl. No. 13/140,714.
U.S. Final Office Action, dated Oct. 7, 2016, issued in U.S. Appl. No. 13/550,374.
U.S. Office Action (Restriction Requirement), dated Feb. 3, 2017, issued in U.S. Appl. No. 14/772,740.
European Extended Search Report dated Jul. 27, 2016 issued in Application No. EP 14 760 467.2.
Berry et al. (2003) "Functionalization of magnetic nanoparticles for applications in biomedicine," *J. Phys. D: Appl. Phys.*, R198-206, 10pp.
Dietrich et al., (2001) "Effects of Particle Size and Molecular Weight of Polyethylenimine on Properties of Nanoparticulate Silicon Dispersions," *J. Am. Ceram. Soc.*, 84(4):806-812.
Fortin et al., (2007) "Size-Sorted Anionic Iron Oxide Nanomagnets as Colloidal Mediators for Magnetic Hyperthermia," *J. Am. Chem. Soc.*, 129(9):2628-2635.
Fritze et al., (2006) "Remote loading of doxorubicin into liposomes driven by transmembrane phosphate gradient," *Biochimica et Biophysica Acta (BBA)—Biomembranes*, Elsevier, Amsterdam, NL, 1758(10):1633-1640.
Guiotto et al., (2004) "Synthesis, Characterization, and Preliminary in Vivo Tests of New Poly(ethylene glycol) Conjugates of the Antitumor Agent 10-Amino-7-ethylcamptothecin" J. Med. Chem., 47(5):1280-1289 [Abstract—2pages].
Liu et al., (2009) "Porous Nanoparticle Supported Lipid Bilayers (Protocells) as Delivery Vehicles," *Journal of the American Chemical Society*, 131(4)1354-1355.
Mock, (1995) "Cucurbituril," *Top. Curr. Chem.*, 175:1-24.
Park et al., (2007) "Controlled Release of Guest Molecules from Mesoporous Silica Particles Based on a pH-Responsive Polypseudorotaxane Motif," *Angew. Chem. Int. Ed.*, 46:1455-1457.
Saha et al., (2007) "Nanovalves," *Adv. Funct. Mater.*, 17:685-693.
Wang et al., (2002) "Gene Expression Profiling in Multidrug Resistant KB Cells Using CDNA Microarrays," *Chinese J. Cancer Res.*, 14(1):5-10.
Weissleder, (2000) "In vivo magnetic resonance imaging of transgene expression," *Nat. Med.*, 6(3):351-354.
Yiu et al. (2007) "A triple-layer design for polyethyleneimine-coated, nanostructured magnetic particles and their use in DNA binding and transfection," *Nanotechnology*, 18:1-6.
U.S. Final Office Action, dated Mar. 7, 2017, issued in U.S. Appl. No. 13/428,830.
Mock et al., (1990) "A Cucurbituril-based Molecular Switch," *Journal of the Chemical Society, Chemical Communications*, 21:1509-1511.
Slowing et al., (2006) "Effect of Surface Functionalization of MCM-41-Type Mesoporous Silica Nanoparticles on the Endocytosis by Human Cancer Cells—Supporting Information," *J. Am. Chem. Soc.*, 11 pages.
Yin et al., (2015) "How does fluorescent labeling affect the binding kinetics of proteins with intact cells?," *Biosens Bioelectron.*, 66:412-416 [HHS Public Access—Author manuscript—11 pages].

\* cited by examiner

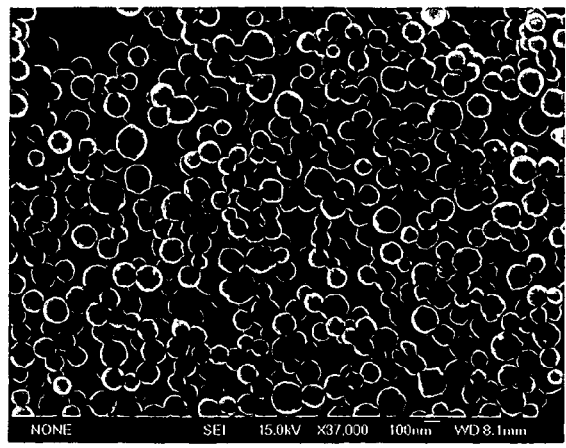
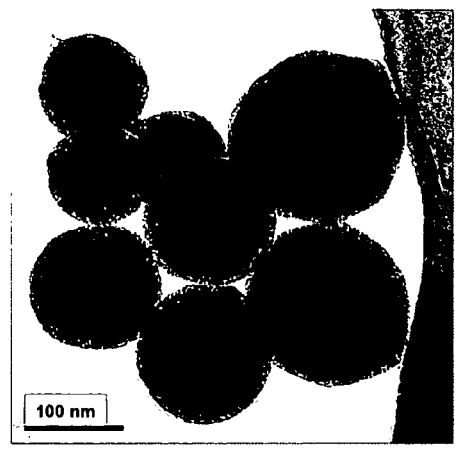
Figure 3A      Figure 3B
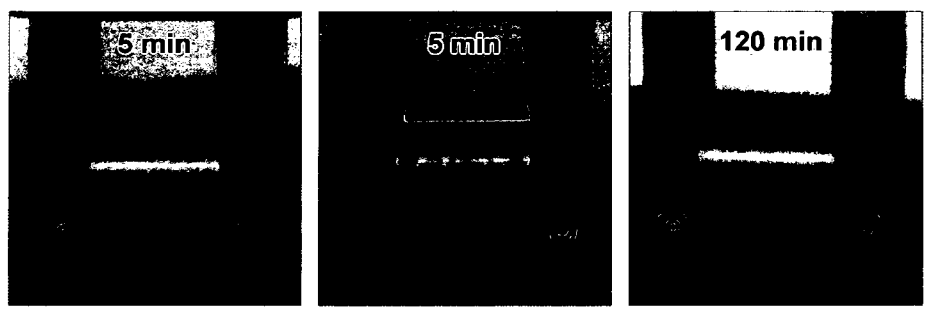
Figure 4

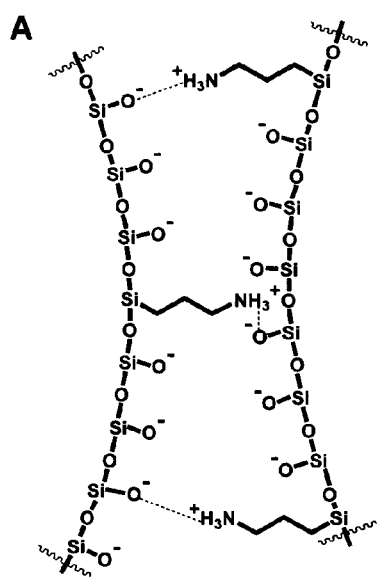
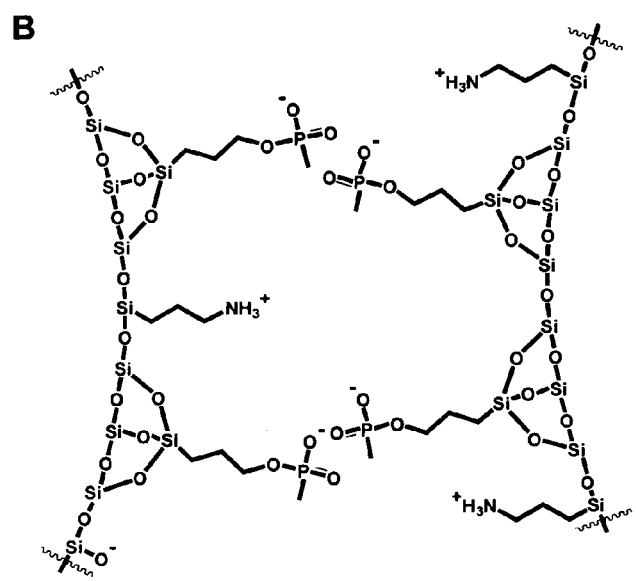
Figure 13A                    Figure 13B

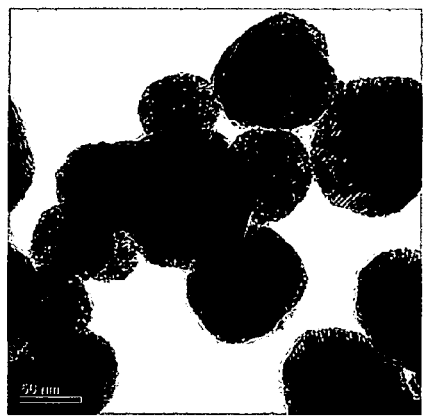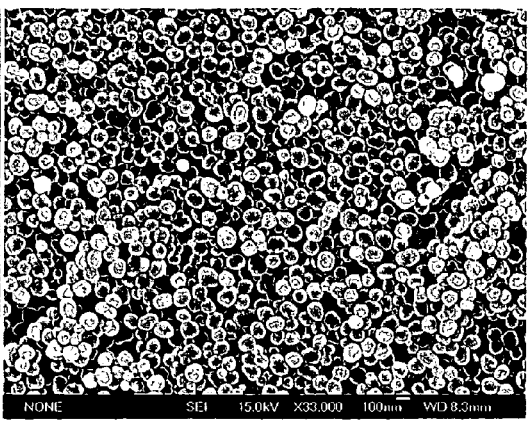
Figure 18A          Figure 18B
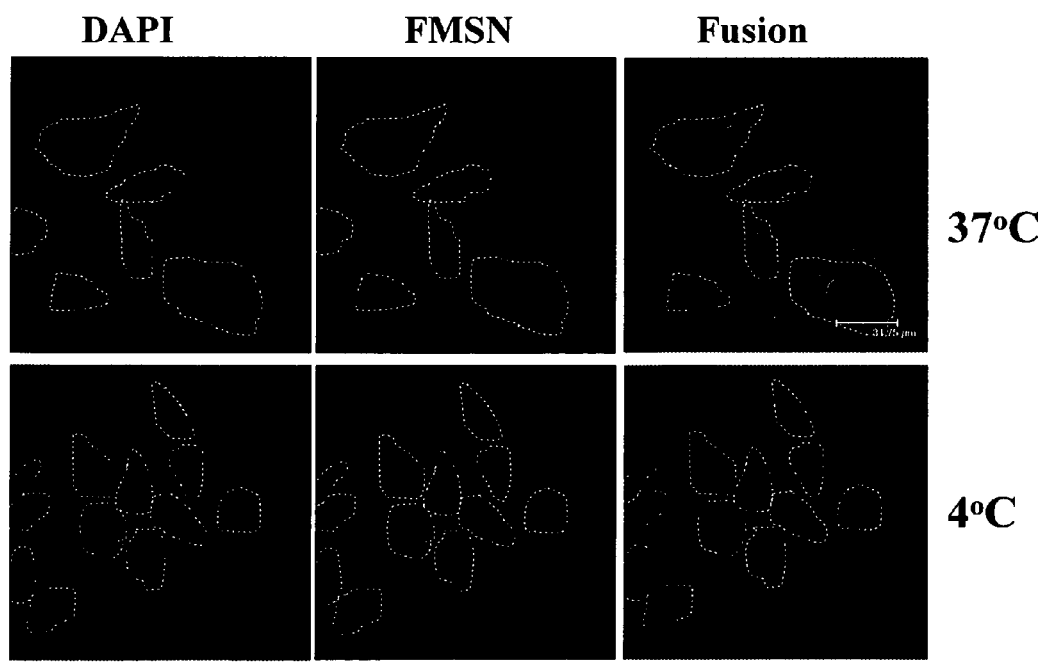
Figure 20

MESOPOROUS SILICA NANOPARTICLES FOR BIOMEDICAL APPLICATIONS

CROSS-REFERENCE OF RELATED APPLICATION

This application claims priority to U.S. Provisional Application No. 60/996,827 filed Dec. 6, 2007, the entire contents of which are hereby incorporated by reference, and is a U.S. national stage application under 35 U.S.C. § 371 of PCT/US2008/013476 filed Dec. 8, 2008, the entire contents of which are incorporated herein by reference.

This invention was made with Government support of Grant No. CA032737 awarded by the National Institutes of Health, and Grant Nos. 0346601 and 0507929 awarded by the National Science Foundation. The Government has certain rights in this invention.

BACKGROUND

1. Field of Invention

The current invention relates to mesoporous silica nanoparticles, and more particularly to mesoporous silica nanoparticles adapted for biomedical applications.

2. Discussion of Related Art

There has been recent rapid progress in utilizing inorganic nanoparticles for biomedical applications due to the extensive amount of work done in the synthesis and modification of the materials (Georganopoulou, D. G.; Chang, L.; Nam, J.-M.; Thaxton, C. S.; Mufson, E. J.; Klein, W. L.; Mirkin, C. A. Nanoparticle-Based Detection in Cerebral Spinal Fluid of a Soluble Pathogenic Biomarker for Alzheimer's Disease. *Proc. Natl. Acad. Sci. USA* 2005, 102, 2273-2276; Gao, X.; Cui, Y.; Levenson, R. M.; Chung, L. W. K.; Nie, S. In Vivo Cancer. Targeting and Imaging with Semiconductor Quantum Dots. *Nat. Biotechnol.* 2004, 22, 969-976; Wu, X.; Liu, H.; Liu, J.; Haley, K. N.; Treadway, J. A.; Larson, J. P.; Ge, N.; Peale, F.; Bruchez, M. P. Immunofluorescent Labeling of Cancer Marker Her2 and Other Cellular Targets with Semiconductor Quantum Dots. *Nat. Biotechnol.* 2002, 21, 41-46; Lee, J.-H.; Huh, Y.-M.; Jun, Y.-W.; Seo, J.-W.; Jang, J.-T.; Song, H.-T.; Kim, S.; Cho, E.-J.; Yoon, H.-G.; Suh, J.-S. et al. Artificially Engineered Magnetic Nanoparticles for Ultra-Sensitive Molecular Imaging. *Nat. Med.* 2007, 13, 95-99; Na, H. B.; Lee, J. H.; An, K.; Park, Y. I.; Park, M.; Lee, I. S.; Nam, D.-H.; Kim, S. T.; Kim, S.-H.; Kim, S.-W. et al. Development of a T1 Contrast Agent for Magnetic Resonance Imaging Using MnO Nanoparticles. *Angew. Chem., Int. Ed.* 2007, 46, 5397-5401; Slowing, I. I.; Trewyn, B. G.; Lin, V. S.-Y. Mesoporous Silica Nanoparticles for Intracellular Delivery of Membrane-Impermeable Proteins. *J. Am. Chem. Soc.* 2007, 129, 8845-8849). These nano-sized materials provide a robust framework in which two or more components can be incorporated to give multifunctional capabilities. An example can be seen in gold nanomaterials: the ability to control the size and shape of the particles and their surface conjugation with antibodies allow for both selective imaging and photothermal killing of cancer cells by using light with longer wavelengths for tissue penetration (Huang, X.; El-Sayed, I. H.; Qian, W.; El-Sayed, M. A. Cancer Cell Imaging and Photothermal Therapy in the Near-Infrared Region by Using Gold Nanorods. *J. Am. Chem. Soc.* 2006, 128, 2115-2120; Chen, J.; Wang, D.; Xi, J.; Au, L.; Siekkinen, A.; Warsen, A.; Li, Z. Y.; Zhang, H.; Xia, Y.; Li, X. Immuno Gold Nanocages with Tailored Optical Properties for Targeted Photothermal Destruction of Cancer Cells. *Nano Lett.* 2007, 7, 1318-1322; Gobin, A. M.; Lee, M. H.; Halas, N. J.; James, W. D.; Drezek, R. A.; West, J. L. Near-Infrared Resonant Nanoshells for Combined Optical Imaging and Photothermal Cancer Therapy. *Nano Lett.* 2007, 7, 1929-1934). Similar success was also demonstrated with polymer-coated superparamagnetic iron oxide nanoparticles. By conjugating multiple components such as fluorescent molecules, tumor-targeting moieties, anticancer drugs, or siRNA to the polymeric coating, not only can these multifunctional nanoparticles target human cancers, they can also be imaged inside the body by both magnetic resonance (MR) and fluorescence imaging (Kohler, N.; Sun, C.; Fichtenholtz, A.; Gunn, J.; Fang, C.; Zhang, M. Methotrexate-Immobilized Poly(ethylene glycol) Magnetic Nanoparticles for MR Imaging and Drug Delivery. *Small* 2006, 2, 785-792; Medarova, Z.; Pham, W.; Farrar, C.; Petkova, V.; Moore, A. In Vivo Imaging of siRNA Delivery and Silencing in Tumors. *Nat. Med.* 2007 13, 372-377). The capability to simultaneously image and treat tumors with nanoparticles may prove advantageous over conventional chemotherapy. Therefore, there is thus a need for improved nanoparticles for use in biological systems.

SUMMARY

A submicron structure according to some embodiments of the current invention includes a silica body defining a plurality of pores that are suitable to receive molecules therein, the silica body further defining an outer surface between pore openings of said plurality of pores; and a plurality of anionic molecules attached to the outer surface of the silica body. The anionic molecules provide hydrophilicity to the submicron structure and are suitable to provide repulsion between other similar submicron structures, and the submicron structure has a maximum dimension less than one micron.

A composition for medical treatment according to some embodiments of the current invention includes a plurality of mesoporous silica nanoparticles, wherein each mesoporous silica nanoparticle of the plurality of mesoporous silica nanoparticles defines a plurality of pores therein. The composition for medical treatment also includes a hydrophobic biologically active material disposed within a plurality of the pores of the plurality of mesoporous silica nanoparticles.

A composition for use on biological cells according to some embodiments of the current invention includes a plurality of mesoporous silica nanoparticles, wherein each mesoporous silica nanoparticle of the mesoporous silica nanoparticles comprises a plurality of anionic molecules attached thereto.

BRIEF DESCRIPTION OF THE DRAWINGS

Further objectives and advantages will become apparent from a consideration of the description, drawings, and examples.

FIG. 3A shows a scanning electron microscope image of the iron oxide incorporated within the mesoporous silica NPs according to an embodiment of the current invention.

FIG. 3B shows a transmission electron microscope image of the iron oxide incorporated within the mesoporous silica NPs according to an embodiment of the current invention.

FIG. 4 shows aqueous suspension of NPs modified with phosphonate (b) compared with those of calcined NPs (a) and NPs without phosphonate (c). After the NPs were dried, they were redispersed in water (5 mg/mL), sonicated thoroughly, and placed next to the magnet. Unlike the other two NPs (a and c), the phosphonate-modified NPs (b) were highly dispersed in the solution and remained suspended even in the presence of the magnetic field. After a longer period of time, the phosphonate-modified NPs were collected by the magnet (right).

FIG. 12A shows scanning electron microscope (left) and transmission electron microscope images of the FMSN (right). FIG. 12B demonstrates that the nanoparticles show the typical XRD patterns of MCM-41 type hexagonal mesoporous silica.

FIG. 13A shows aggregation between the nanoparticles was caused by the interparticle hydrogen bonding between the surface silanol groups and the amine groups.

FIG. 13B shows that surface modification with THMP increased the electrostatic repulsion between the nanoparticles and decreased the aggregation.

FIG. 14A Upper panels: normal microscopic images of PANC-1 cells; lower panels: fluorescent microscopic images after the indicated hours. Similar results were observed in other cell lines (data not shown); FIG. 14B PANC-1 cells stained with Acridine Orange (left) and the fluorescence of the nanoparticles within the same cell (right). FIG. 14C PANC-1 cells stained with lysoSensor green DND-189 (left) and the fluorescence of the nanoparticles within the same cell (right). FIG. 14D Fluorescence of CPT after the cells were incubated with CPT-loaded FMSN (right) for 3 hours. No fluorescence was observed within the cells that were incubated with suspension of CPT in PBS (left).

FIGS. 18A and 18B show characterization of FMSN. FIG. 18A: Transmission electron microscopy image and FIG. 18B: Scanning electron microscopy image (SEM) of FMSN.

FIG. 19A: PANC-1 cells stained with Acridine Orange (left) and the fluorescence of the nanoparticles within the same cell (right). The red fluorescence showed the location of lysosomes. FIG. 19B: After incubation of Hepa-1 cells with FMSN for 3 h, location of FMSN was compared with that of LAMP1 that was determined by using anti-mouse monoclonal antibody (1D4B) and secondary antibody (Alexa-594 goat anti-rat IgG). Nuclei were stained with DAPI.

FIG. 20 shows confocal laser scanning microscopy images of FMSN taken up by cancer cells. PANC-1 cells were incubated at 37° C. or 4° C. for 30 min, and then the uptake was examined. Nuclei were stained with DAPI. Left panel: nuclei; middle panel: FMSN; right panel: merged image. Cell periphery is indicated by dotted lines.

FIG. 22A: PANC-1 cells were treated with empty FMSN in PBS (▲), paclitaxel in DMSO (■), paclitaxel in $H_2O$ (●) or paclitaxel-loaded FMSN in PBS (X), and the percentage of viable cells was compared to control wells without treatment (Y-axis). The concentration of FMSN is shown on top of each figure (μg/ml), while that of paclitaxel in DMSO, in PBS, or loaded in FMSN (μg/ml), is shown under each figure (nM). FIG. 22B: Representative images of PANC-1 cells. PANC-1 cells were treated with (a) 1.15 μg/ml of empty FMSN, (b) 1 nM paclitaxel in DMSO, (c) 1 nM paclitaxel in $H_2O$, or (d) 1.15 mg/ml of paclitaxel-loaded FMSN for 24 h, and then were observed with light microscopy.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
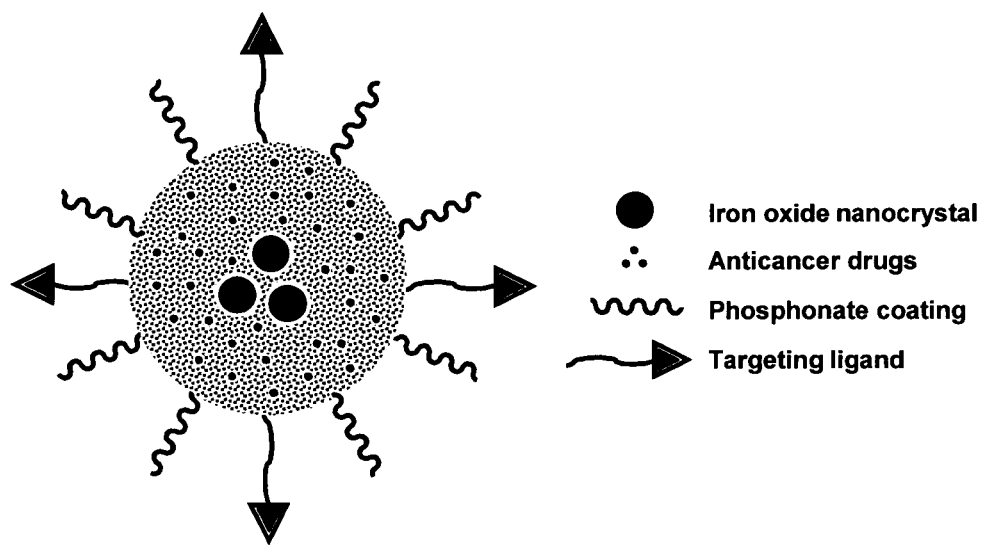
FIG. 1 is a Schematic illustration of multifunctional nanoparticles according to an embodiment of the current invention showing iron oxide nanocrystals encapsulated within a mesoporous silica body, hydrophobic anticancer drugs stored inside pores of the silica body, and surface modifications with phosphonate and folic acid targeting ligands.

FIG. 1 is a schematic illustration of a submicron structure according to an embodiment of the current invention. The submicron structure includes a silica body that defines a plurality of pores therein. For example, the silica body can be a mesoporous silica nanoparticle. The fact that we refer to the body as a silica body does not preclude materials other than silica from also being incorporated within the silica body. The plurality of pores defined by the silica body is suitable to receive molecules therein. For example, one or more pharmaceutical molecules may be disposed within the pores. However, general aspects of the invention are not limited to only pores that can receive pharmaceutical molecules. For example, the pores can be suitable to receive therapeutic molecules, RNA, DNA, or portions thereof, or any other suitably small molecules that may be desirable to deliver to biological cells. In some embodiments, the silica body may be substantially spherical with a plurality of pore openings through the surface providing access to the pores. However, the silica body can have shapes other than substantially spherical shapes in other embodiments of the current invention. Generally, the silica body defines an outer surface between the pore openings, as well as side walls within the pores. The pores can extend through the silica body to another pore opening, or can extend only partially through the silica body such that it has a bottom surface of the pore defined by the silica body. The submicron structure can also have a plurality of anionic molecules attached to the outer surface of the silica body. FIG. 1 illustrates schematically an embodiment in which the plurality of anionic molecules are phosphonate moieties attached to the outer surface of the silica body to effectively provide a phosphonate coating on the silica body of the submicron structure. For example, the anionic molecules can be trihydroxysilylpropyl methylphosphonate molecules according to an embodiment of the current invention.

The phosphonate coating to the silica body can provide an important role in the delivery of hydrophobic cancer drugs to cancer cells in some embodiments of the current invention. This phosphonate coating can provide a negative zeta potential that is responsible for electrostatic repulsion to keep such submicron structures dispersed in an aqueous tissue culture medium. This dispersion can also be important for keeping the particle size limited to a size scale that allows endocytic uptake. In addition to size considerations, the negative zeta potential likely also plays an important role in the formation of a protein corona on the particle surface that can further assist cellular uptake. We are currently identifying specific proteins but it is possible that this could include molecules such as albumin, transferrin or other serum proteins that could participate in receptor-mediated uptake. In addition to the role of the phosphonate coating for successful drug delivery, it can also provide beneficial effects for our method of soaking hydrophobic anti-cancer drugs, such as campthothecin and taxol, into the particle pores before allowing the particles to dry according to some embodiments of the current invention. Drying of the particles before the addition of aqueous medium, results in hydrophobic repulsion, thereby generating phase separation that can stably trap the campthothecin and taxol in the pores. This can allow these particles to act as stable carriers in aqueous medium and for these agents to be delivered into the cell encapsulated in the particles according to some embodiments of the current invention. Drug release in the cell involves an unknown mechanism. One possibility is that the release takes place in the hydrophobic interior of the surface lipid bilayer. Thus, a phosphonate coating on the silica body can provide advantages for methods of loading hydrophobic anticancer drugs into the submicron structures as well as for cellular uptake according to some embodiments of the current invention.

The submicron structures according to some embodiments of the current invention may be referred to as nanoparticles. The term nanoparticles as used herein is intended the include particles as large as 300 nm. For particles larger than 300 nm, they become ineffective in entering living cells. On the other hand, nanoparticles smaller than 50 nm become less useful for transporting molecules loaded in the pores into biological cells. Furthermore, for drug delivery according to some embodiments of the current invention, mesoporous silica nanoparticles of at least about 50 nm and less than about 150 nm were found to work well.

The outer surface of the silica body of the submicron structure can also be functionalized with molecules in additional to anionic molecules according to some embodiments of the current invention. For example, a plurality of folate ligands can be attached to the outer surface of the silica body of the submicron nanostructure according to some embodiments of the current invention, as is illustrated schematically in FIG. 1.

In some embodiments of the current invention, the submicron structure may also include fluorescent molecules attached to the silica body. For example, fluorescent molecules may be attached inside the pores of the silica body in some embodiments of the current invention. For example, the fluorescent molecules can be an amine-reactive fluorescent dye attached by being conjugated with an amine-functionalized silane according to some embodiments of the current invention. Examples of some fluorescent molecules, without limitation, can include fluorescein isothiocyanate, NHS-fluorescein, rhodamine B isothiocyanate, tetramethylrhodamine B isothiocyanate, and/or Cy5.5 NHS ester.

In further embodiments of the current invention, the submicron structures may further comprise one or more nanoparticle of magnetic material formed within said silica body of said submicron structure, as is illustrated schematically in FIG. 1 for one particular embodiment. For example, the nanoparticles of magnetic material can be iron oxide nanoparticles according to an embodiment of the current invention. However, the broad concepts of the current invention are not limited to only iron oxide materials for the magnetic nanoparticles. Such nanoparticles of magnetic material incorporated in the submicron structures can permit them to be tracked by magnetic resonance imaging (MRI) systems and/or manipulated magnetically.

In further embodiments of the current invention, the submicron structures may further comprise one or more nanoparticle of a material that is optically dense to x-rays. For example, gold nanoparticles may be formed with the silica body of the submicron structures according to some embodiments of the current invention.

Further embodiments of the current invention include compositions that include a plurality of nanostructures according to the current invention. In some embodiments, the nanostructures may have molecules loaded in at least some of the pores of the nanostructures. The molecules can be pharmaceuticals in some embodiments; however, other types of molecules may be used in other embodiments of the current invention. In some embodiments, a composition including the nanostructures may be loaded with hydrophobic drugs, for example drugs for cancer treatment such as camptothecin, paclitaxel, resveratrol, etoposide and/or carmustine.

Example 1

In following examples according to some embodiments of the current invention, we describe the synthesis of multifunctional inorganic nanoparticles that are designed for cancer cell-specific delivery of hydrophobic anticancer drugs that also have dual-imaging capability (optical and MR) (FIG. 1). Superparamagnetic iron oxide nanocrystals (20 nm) were incorporated in the mesoporous silica nanoparticles (100-200 nm) for the magnetic manipulation and MR imaging. Surface attachment with hydrophilic groups increased the stability of the nanoparticle dispersion in aqueous solution. The mesoporous silicate was further modified with fluorescent molecules and targeting ligands, and the pores were filled with chemotherapeutic drug molecules.

In this example, we demonstrate that these nanoparticles can be monitored inside living cells by both MR and fluorescence imaging methods, and simultaneously used as a drug delivery vehicle. The targeting ligand modification increased the drug payload delivery into human cancer cells relative to that into non-cancerous cells. The synthetic procedures require inexpensive and non-hazardous precursors and are simple enough for large-scale production. The potential to simultaneously monitor and deliver molecules to the targeted tissue region can be highly beneficial for both imaging and therapeutic purposes.

Results and Discussion

Magnetic Functionality.

Figure 2:
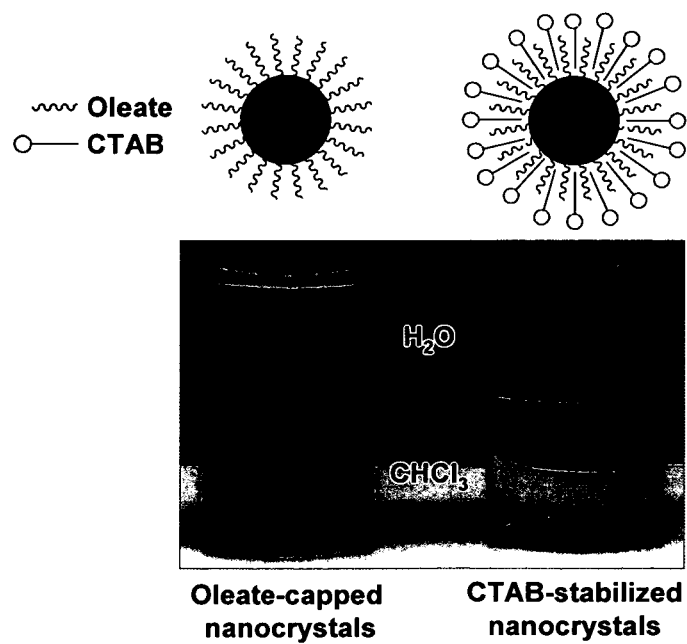
FIG. 2 shows (Left) as-synthesized oleate-capped iron oxide nanocrystals in chloroform and (right) water-soluble CTAB-stabilized nanocrystals according to an embodiment of the current invention.

Superparamagnetic iron oxide nanocrystals were used as the functional component that can provide the MR imaging and magnetic manipulation capabilities. We followed the high-temperature and non-aqueous route to synthesize the magnetic nanoparticles in order to produce highly uniform and crystalline particles (Jana, N. R.; Chen, Y.; Peng, X. Size- and Shape-Controlled Magnetic (Cr, Mn, Fe, Co, Ni) Oxide Nanocrystals via a Simple and General Approach. *Chem. Mater.* 2004, 16, 3931-3935; Park, J.; An, K.; Hwang, Y.; Park, J.-G.; Noh, H.-J.; Kim, J.-Y.; Park, J.-H.; Hwang, N.-M.; Hyeon, T. Ultra-Large-Scale Syntheses of Monodisperse Nanocrystals. *Nat. Mater.* 2004, 3, 891-895; Sun, S.; Zeng, H.; Robinson, D. B.; Raoux, S.; Rice, P. M.; Wang, S. X.; Li, G. Monodisperse $MFe_2O_4$ (M=Fe, Co, Mn) Nanoparticles. *J. Am. Chem. Soc.* 2004, 126, 273-279; Yu, W. W.; Falkner, J. C.; Yavuz, C. T.; Colvin, V. L. Synthesis of Monodisperse Iron Oxide Nanocrystals by Thermal Decomposition of Iron Carboxylate Salts. *Chem. Commun.* 2004, 2306-2307; Jun, Y. W.; Huh, Y. M.; Choi, J. S.; Lee, J. H.; Song, H. T.; Kim, S. J.; Yoon, S.; Kim, K. S.; Shin, J. S.; Suh, J. S. et al. Nanoscale Size Effect of Magnetic Nanocrystals and Their Utilization for Cancer Diagnosis via Magnetic Resonance Imaging. *J. Am. Chem. Soc.* 2005, 127, 5732-5733). The nanocrystals were synthesized by the thermal decomposition of iron-oleate complexes in a solution of oleic acid surfactants and octadecene solvent because this facile procedure utilizes inexpensive reagents and yields large quantities of the materials (Park, J.; An, K.; Hwang, Y.; Park, J.-G.; Noh, H.-J.; Kim, J.-Y.; Park, J.-H.; Hwang, N.-M.; Hyeon, T. Ultra-Large-Scale Syntheses of Monodisperse Nanocrystals. *Nat. Mater.* 2004, 3, 891-895). The hydrophobic nanocrystals dissolved in chloroform were transferred to the water phase by mixing them with an aqueous cetyltrimethylammonium bromide (CTAB) solution and evaporating the organic solvent (Fan, H.; Yang, K.; Boye, D. M.; Sigmon, T.; Malloy, K. J.; Xu, H.; Lopez, G. P.; Brinker, C. J. Self-Assembly of Ordered, Robust, Three-Dimensional Gold Nanocrystal/Silica Arrays. *Science* 2004, 304, 567-571; Fan, H.; Gabaldon, J.; Brinker, C. J.; Jiang, Y.-B. Ordered Nanocrystal/Silica Particles Self-Assembled from Nanocrystal Micelles and Silicate. *Chem. Commun.* 2006, 2323-2325; Kim, J.; Lee, J. E.; Lee, J.; Yu, J. H.; Kim, B. C.; An, K.; Hwang, Y.; Shin, C.-H.; Park, J.-G.; Hyeon, T. Magnetic Fluorescent Delivery Vehicle Using Uniform Mesoporous Silica Spheres Embedded with Monodisperse Magnetic and Semiconductor Nanocrystals. *J. Am. Chem. Soc.* 2006, 128, 688-689). Using this simple method, the hydrophobic tail of the CTAB surfactant interacts strongly with the hydrophobic oleate ligand on the surface of the nanocrystals and the hydrophilic charged head group of CTAB makes the nanocrystals water-soluble. The transfer of the nanocrystals into aqueous solution was highly effective since there were no visible precipitates or aggregates in the solution (FIG. 2).

Mesoporous Silica Formation.

Silica can offers many advantages as the framework for a multifunctional nanoparticle. In addition to being able to incorporate other inorganic materials within or on the surface of the framework (Jiang, X.; Brinker, C. J. Aerosol-Assisted Self-Assembly of Single-Crystal Core/Nanoporous Shell Particles as Model Controlled Release Capsules. *J. Am. Chem. Soc.* 2006, 128, 4512-4513; Lee, J.-H.; Jun, Y.-w.; Yeon, S.-I.; Shin, J.-S.; Cheon, J. Dual-Mode Nanoparticle Probes for High-Performance Magnetic Resonance and Fluorescence Imaging of Neuroblastoma. *Angew. Chem., Int. Ed.* 2006, 118, 8340-8342; Lin, Y. S.; Wu, S. H.; Hung, Y.; Chou, Y. H.; Chang, C.; Lin, M. L.; Tsai, C. P.; Mou, C. Y. Multifunctional Composite Nanoparticles: Magnetic, Luminescent, and Mesoporous. *Chem. Mater.* 2006, 18, 5170-5172), a variety of functional molecules can be attached to the silica surface via silane linkers (Wang, L.; Zhao, W.; O'Donoghue, M. B.; Tan, W. Fluorescent Nanoparticles for Multiplexed Bacteria Monitoring. *Bioconjugate Chem.* 2007, 18, 297-301).

Mesoporous silica spheres (100-200 nm) were synthesized around the iron oxide nanocrystals by following the modified procedures described by Kim et al. and Fan et al. In this procedure, the silica source tetraethylorthosilicate (TEOS) was added into the aqueous solution containing CTAB-coated nanocrystals, CTAB, and sodium hydroxide. The interaction between the hydrolyzed TEOS molecules with the CTAB-coated nanocrystals and the free surfactant micelles helped promote the base-catalyzed condensation of TEOS to form the mesostructure. The morphology of the iron oxide-mesoporous silica nanoparticles (NPs) is highly dependent upon the temperature of the solution. When the temperature was too low (<65° C.), slow silica formation resulted in larger-sized materials which consisted of mostly structured mesoporous silica particles with the iron oxide clusters situated on the edges of the silica particles. As a result, it was necessary to form the NPs at higher temperature, vigorous stirring, and dilute precursor solution, all of which have been used to synthesize mesostructured particles in the nanometer range (Cai, Q.; Luo, Z.-S.; Pang, W.-Q.; Fan, Y.-W.; Chen, X.-H.; Cui, F.-Z. Dilute Solution Routes to Various Controllable Morphologies of MCM-41 Silica with a Basic Medium. *Chem. Mater.* 2001, 13, 258-263; Lin, Y. S.; Tsai, C. P.; Huang, H. Y.; Kuo, C. T.; Hung, Y.; Huang, D. M.; Chen, Y. C.; Mou, C. Y. Well-Ordered Mesoporous Silica Nanoparticles as Cell Markers. *Chem. Mater.* 2005, 17, 4570-4573). However, if the temperature was greater than 80° C., the mesoporous silica tend to coalesce and form large clumps of materials. At the optimum temperature range (65-80° C.), spherical 100-200 nm in diameter NPs were formed (FIGS. 3A and 3B). The transmission electron microscope images show the dark iron oxide nanocrystals at the center of the NPs and also the 2D hexagonal mesoporous silica structure.

The method involving the aqueous transfer of the hydrophobic nanocrystals to the aqueous solution and the synthesis of the nanocrystals-mesoporous silica NPs can be applied to other materials as well. By using this general procedure, we were also able to incorporate gold and silver nanocrystals at the center of the mesoporous silica particles. The hydrophobic dodecanethiol-capped gold nanocrystals (Brust, M.; Walker, M.; Bethell, D.; Schiffrin, D. J.; Whyman, R. Synthesis of Thiol-Derivatised Gold Nanoparticles in a Two-Phase Liquid-Liquid System. *Chem. Commun.* 1994, 801-802) and oleylamine-capped silver nanocrystals (Hiramatsu, H.; Osterloh, F. E. A Simple Large-Scale Synthesis of Nearly Monodisperse Gold and Silver Nanoparticles with Adjustable Sizes and with Exchangeable Surfactants. *Chem. Mater.* 2004, 16, 2509-2511) were first coated with CTAB by using similar procedures.

Fluorescent dye molecules were functionalized onto the iron-oxide mesoporous silica NPs using co-condensation method. Fluorescein isothiocyanate was first conjugated with aminopropyltriethoxysilane and the product, along with TEOS, was then added into the solution containing the starting precursors in order to incorporate fluorescein along the pore walls and particle surface (Lin, Y. S.; Tsai, C. P.; Huang, H. Y.; Kuo, C. T.; Hung, Y.; Huang, D. M.; Chen, Y. C.; Mou, C. Y. Well-Ordered Mesoporous Silica Nanoparticles as Cell Markers. *Chem. Mater.* 2005, 17, 4570-4573; Slowing, I.; Trewyn, B. G.; Lin, V. S.-Y. Effect of Surface Functionalization of MCM-41-Type Mesoporous Silica Nanoparticles on the Endocytosis by Human Cancer Cells. *J. Am. Chem. Soc.* 2006, 128, 14792-14793; Lu, J.; Liong, M.; Zink, J. I.; Tamanoi, F. Mesoporous Silica Nanoparticles as a Delivery System for Hydrophobic Anticancer Drugs. *Small* 2007, 3, 1341-1346). This modification to the particles introduced the fluorescence functionality without affecting the size and shape of the materials, and enabled the cellular uptake of the NPs to be monitored by fluorescence microscopy.

Pore Characterization.

In order to load cargo molecules such as drugs into the NPs, the structure-directing CTAB surfactants must be removed from the mesopores. The typical methods of either calcining or heating the materials in acidic alcohol to extract the surfactants were not suitable. Calcination not only destroys the fluorescent dyes along with any organic surface modifications, but it also causes irreversible particle aggregation, which makes the materials poorly dispersible in water (FIG. 4). Solvent extraction with a mixture of alcohol and hydrochloric acid dissolves the iron oxide nanocrystals (Yi, D. K.; Lee, S. S.; Papaefthymiou, G. C.; Ying, J. Y. Nanoparticle Architectures Templated by $SiO_2$—$Fe_2O_3$ Nanocomposites. *Chem. Mater.* 2006, 18, 614-619). To circumvent these problems, an ion exchange procedure using ammonium nitrate was used to remove the surfactants from the materials as confirmed by the FTIR spectra (Lin, Y. S.; Wu, S. H.; Hung, Y.; Chou, Y. H.; Chang, C.; Lin, M. L.; Tsai, C. P.; Mou, C. Y. Multifunctional Composite Nanoparticles: Magnetic, Luminescent, and Mesoporous. *Chem. Mater.* 2006, 18, 5170-5172; Lang, N.; Tuel, A. A Fast and Efficient Ion-Exchange Procedure To Remove Surfactant Molecules from MCM-41 Materials. *Chem. Mater.* 2004, 16, 1961-1966).

X-ray diffraction (XRD) analysis and nitrogen adsorption-desorption experiments were conducted on the NPs after the CTAB removal to investigate the porosity. Low angle XRD pattern of the solvent-extracted NPs shows a d-spacing of approximately 4 nm. The adsorption-desorption isotherm can be classified as a type IV isotherm according to the IUPAC nomenclature and is typically observed for structured mesoporous materials (Cai, Q.; Luo, Z.-S.; Pang, W.-Q.; Fan, Y.-W.; Chen, X.-H.; Cui, F.-Z. Dilute Solution Routes to Various Controllable Morphologies of MCM-41 Silica with a Basic Medium. *Chem. Mater.* 2001, 13, 258-263; Grün, M.; Lauer, I.; Unger, K. K. The Synthesis of Micrometer- and Submicrometer-Size Spheres of Ordered Mesoporous Oxide MCM-41. *Adv. Mater.* 1997, 9, 254-257). The Barret-Joyner-Halenda (BJH) method was used to calculate the pore size distribution, yielding an average calculated pore diameter of approximately 3 nm.

Aggregation of Particles.

We have shown that mesoporous silica can store water-insoluble drugs within the pores without releasing them in aqueous solution due to the hydrophobic nature of the molecules (Lu, J.; Liong, M.; Zink, J. I.; Tamanoi, F. Mesoporous Silica Nanoparticles as a Delivery System for Hydrophobic Anticancer Drugs. *Small* 2007, 3, 1341-1346). In order to load the hydrophobic molecules into the pores, the particles were suspended in a DMSO solution of the molecules. When the iron oxide-mesoporous silica NPs were taken out of the DMSO suspension, dried, and added to water, they became poorly dispersed and settled to the bottom quickly. This irreversible aggregation is caused by the interparticle hydrogen bonding interaction between the surface silanol groups and can be prevented by grafting hydrophilic molecules on the surfaces (Xu, H.; Yan, F.; Monson, E. E.; Kopelman, R. Room-Temperature Preparation and Characterization of Poly(ethylene glycol)-Coated Silica Nanoparticles for Biomedical Applications. *J. Biomed Mater. Res., Part A* 2003, 66A, 870-879; Zhang, Z.; Berns, A. E.; Willbold, S.; Buitenhuis, J. Synthesis of Poly(ethylene glycol) (PEG)-Grafted Colloidal Silica Particles with Improved Stability in Aqueous Solvents. *J. Colloid Interface Sci.* 2007, 310, 446-455; Gerion, D.; Pinaud, F.; Williams, S. C.; Parak, W. J.; Zanchet, D.; Weiss, S.; Alivisatos, A. P. Synthesis and Properties of Biocompatible Water-Soluble Silica-Coated CdSe/ZnS Semiconductor Quantum Dots. *J. Phys. Chem. B* 2001, 105, 8861-8871; Bagwe, R. P.; Hilliard, L. R.; Tan, W. Surface Modification of Silica Nanoparticles to Reduce Aggregation and Nonspecific Binding. *Langmuir* 2006, 22, 4357-4362). The surfaces of the NPs were modified shortly after the particle formation with hydrophilic trihydroxysilylpropyl methylphosphonate to prevent the interparticle aggregation. The dispersibility of the NPs with or without the phosphonate modification was relatively similar if the materials were constantly suspended in solution. However, once the materials were dried and redispersed in aqueous solution, the difference between the NPs with and without phosphonate modification was noticeable (FIG. 4). Without the surface modification, the NPs aggregated and can easily be collected by the magnet similar to the calcined NPs. The phosphonate-modified NPs, on the other hand, were very stable and remained suspended in the solution. Over a longer period of 2 hours, some of the phosphonate-modified NPs were collected by the neodymium magnet showing that they can be manipulated by an external magnetic field.

Particle Uptake by Cells.

Figure 5:
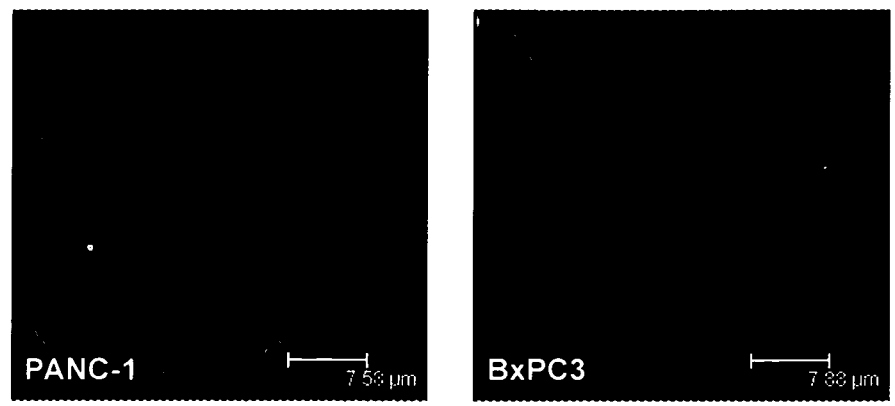
FIG. 5 shows fluorescence microscopy images of the nanoparticle uptake by human pancreatic cancer cells PANC-1 and BxPC3 according to an embodiment of the current invention. The cell membranes (red fluorescence) were stained with WGA and the clusters of NPs (green fluorescence) were modified with FITC.

The cellular uptake of the NPs was confirmed on two different pancreatic cancer cell lines PANC-1 and BxPC3. The NPs were able to enter the cells within 30 min without causing any observed toxicity. As shown in FIG. 5, the clusters of NPs (green fluorescence) were located within the cells and not on the cell membranes (red fluorescence, WGA-Alexa Fluor 594 stain). Additionally, the treated cells were examined cross-sectionally by confocal fluorescence microscopy in order to confirm that the NPs were indeed internalized by the cells and not simply bound on the surface membrane.

MR Imaging.

Figure 6:
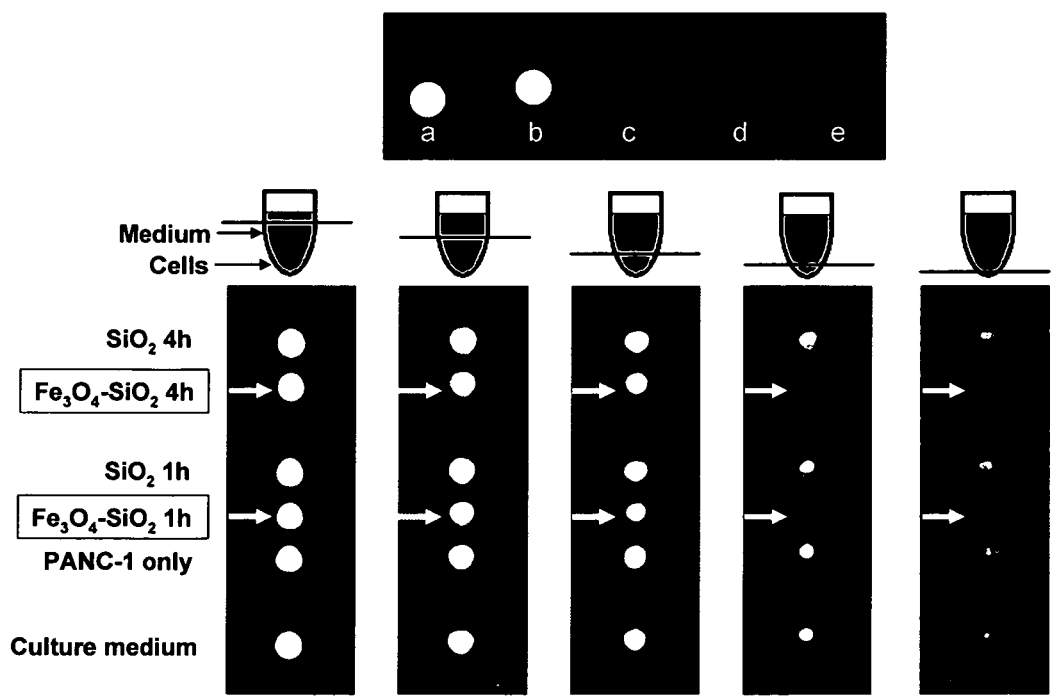
FIG. 6 shows (Top) T2-weighted MR image of (a) water, (b) plain mesoporous silica NPs (2 mg/mL), and iron oxide-mesoporous silica NPs at (c) 4, (d) 2, and (e) 1 mg/mL. (Bottom) Cross section T2-weighted MR images of the centrifuge tubes at different tube heights. PANC-1 cells that were treated with iron-oxide-mesoporous silica NPs (labeled with arrows) appeared dark compared to the other samples.

In order to determine whether these NPs could be used for contrast agents in MR imaging, their contrast effect in solution and inside the cells was tested using a clinical MRI instrument. Different concentrations of the aqueous NPs suspension (1-4 mg/mL) were placed in the centrifuge tubes. For further comparison, plain mesoporous silica NPs (without the iron oxides) were also tested to confirm that it was not the silicate materials that caused the contrast. Superparamagnetic iron oxide nanocrystals are used as contrast agents in MRI because of their negative enhancement effect on the T2-weighted sequences (Corot, C.; Robert, P.; Idee, J.-M.; Port, M. Recent Advances in Iron Oxide Nanocrystal Technology for Medical Imaging. *Adv. Drug Delivery Rev.* 2006, 58, 1471-1504). As a result, the tubes containing the iron-oxide mesoporous silica NPs appeared dark in the T2-weighted MR image (FIG. 6). On the other hand, the tubes which contained the water and the plain mesoporous silica NPs remained bright and indistinguishable.

To observe the contrast effect inside the cells, PANC-1 cells were first treated with the NPs for 1 h or 4 h period before washing and collecting in Dulbecco's modified Eagle's medium (DMEM) in 0.2 mL centrifuge tubes. The control samples consisted of the DMEM, the untreated cells, and the cells treated with plain mesoporous silica NPs. Several T2-weighted images of the cross sections were taken going from the top of the tubes (containing the media) to the bottom of the tubes (containing the cells) (FIG. 6). The tubes containing the control samples were comparable in brightness, whereas the tubes containing the cells treated with the iron oxide-mesoporous silica NPs appeared dark because of the decrease in the T2 relaxation. These results show that the NPs can be used for MR contrast agents in solution and inside the cells.

Drug Delivery.

Figure 7:
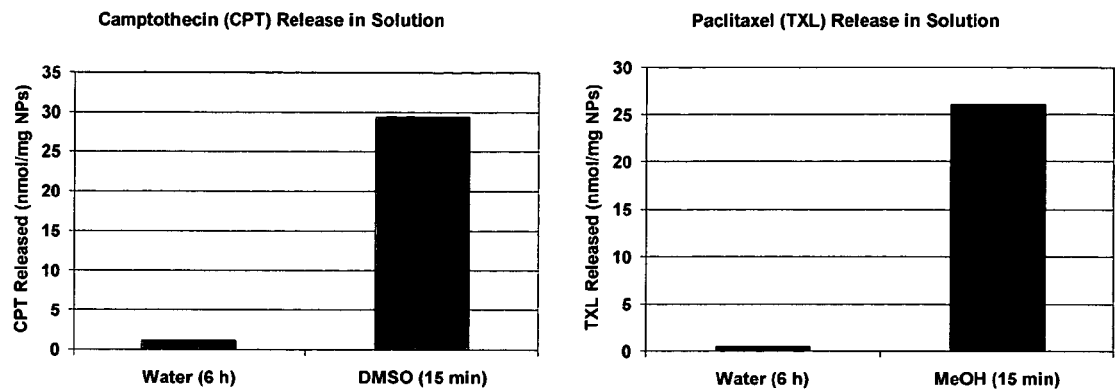
FIG. 7 shows UV/Vis absorption measurements show that most of the water-insoluble drug molecules were trapped inside the pores when the NPs were dispersed in water, but were quickly released in organic solvents.

The NPs were used to store and deliver water-insoluble anticancer drugs into cells. The materials were loaded with either camptothecin (CPT) or paclitaxel (TXL) by soaking them in a concentrated drug-DMSO solution. The drug-loaded NPs were collected by centrifugation to remove the supernatant and dried under vacuum before resuspending them in aqueous solution. By using UV/Vis absorption spectroscopy, it was observed that only 4% of the stored drug molecules were released into the supernatant when the drug-loaded NPs were dispersed in aqueous solution and left in suspension for 6 h. However, once the drug-loaded NPs were again redispersed in DMSO or methanol, all of the drugs came out of the mesopores and were observed in the supernatant (FIG. 7). Based on absorption measurements, approximately 30 nmol of drug molecules were stored inside 1 mg of the NPs.

Figure 8:
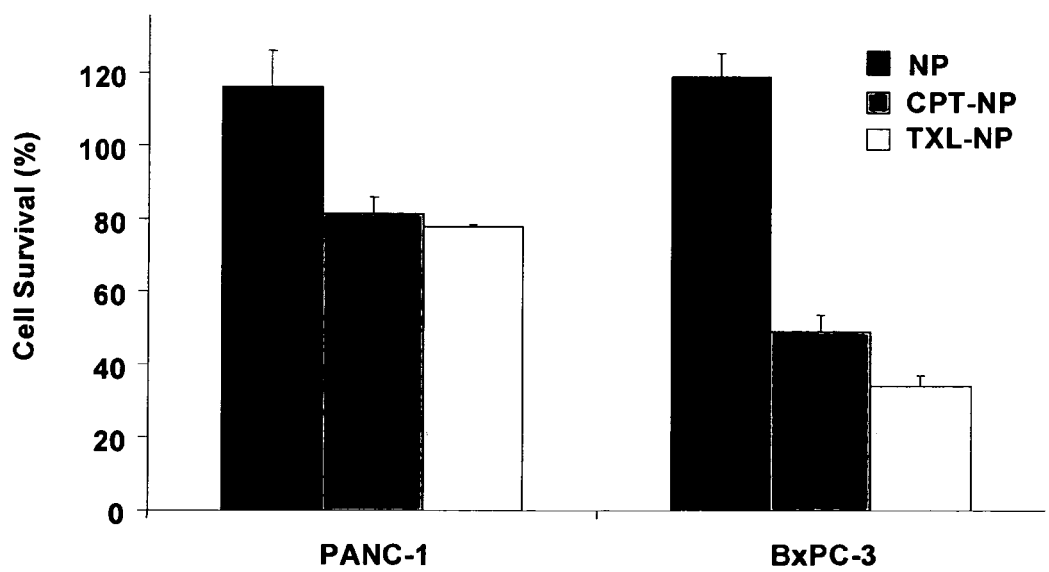
FIG. 8 shows cell growth inhibition assay for the drug-loaded NPs. Human pancreatic cancer cells PANC-1 and BxPC-3 were treated for 24 h with nanoparticles (NP), camptothecin-loaded nanoparticles (CPT-NP), or paclitaxel-loaded nanoparticles (TXL-NP). The concentration of the NPs used was 20 μg/mL.

The efficacy of these drug-loaded NPs was tested on the pancreatic cancer cell lines PANC-1 and BxPC3. The NPs alone were not toxic to the cells at the concentrations used in the experiment, but the drug-loaded NPs caused observable cytotoxicity to both cell lines (FIG. 8). We postulated that the water-insoluble drugs were released from the mesopores when the NPs had entered the cellular membrane. Furthermore, the aqueous suspensions of the drug-loaded NPs were stable for a long period of time since they retained their cytotoxicity after over 2 months of storage at 4° C. Based on these results, the NPs can potentially be used as a vehicle to store and deliver anticancer drugs that are both highly toxic and water-insoluble into different types of cancer cells.

Targeting of Cancer Cells.

Folic acid was used as the targeting component for this study because α-folate receptor is observed to be up-regulated in various types of human cancers (Sudimack, J.; Lee, R. J. Targeted Drug Delivery Via the Folate Receptor. *Adv. Drug Delivery Rev.* 2000, 41, 147-162; Kam, N. W. S.; O'Connell, M.; Wisdom, J. A.; Dai, H. Carbon Nanotubes as Multifunctional Biological Transporters and Near-Infrared Agents for Selective Cancer Cell Destruction. *Proc. Natl. Acad. Sci. USA* 2005, 102, 11600-11605). Since the coating with phosphonate groups was done during the particle synthesis, there still remained many surface silanol groups at the pore orifices after the CTAB had been removed, which can be used for further surface modification (Mal, N. K.; Fujiwara, M.; Tanaka, Y.; Taguchi, T.; Matsukata, M. Photo-Switched Storage and Release of Guest Molecules in the Pore Void of Coumarin-Modified MCM-41. *Chem. Mater.* 2003, 15, 3385-3394; Nguyen, T. D.; Liu, Y.; Saha, S.; Leung, K. C.-F.; Stoddart, J. F.; Zink, J. I. Design and Optimization of Molecular Nanovalves Based on Redox-Switchable Bistable Rotaxanes. *J. Am. Chem. Soc.* 2007, 129, 626-634; Zhu, Y.; Fujiwara, M. Installing Dynamic Molecular Photomechanics in Mesopores: A Multifunctional Controlled-Release Nanosystem. *Angew. Chem., Int. Ed.* 2007, 46, 2241-2244). The amide linkage between the carboxyl group on the folic acid and the amine group on the aminopropyltriethoxysilane was first formed before grafting the folate-silanes onto the surface of the NPs (Slowing, I.; Trewyn, B. G.; Lin, V. S.-Y. Effect of Surface Functionalization of MCM-41-Type Mesoporous Silica Nanoparticles on the Endocytosis by Human Cancer Cells. *J. Am. Chem. Soc.* 2006, 128, 14792-14793; Lee, R. J.; Low, P. S. Delivery of Liposomes into Cultured KB Cells via Folate Receptor-Mediated Endocytosis. *J. Biol. Chem.* 1994, 269, 3198-3204). The same batch of materials were used for the in vitro comparison between the NPs and the folate-modified NPs to avoid the problems in batch-to-batch variability.

Figure 9:
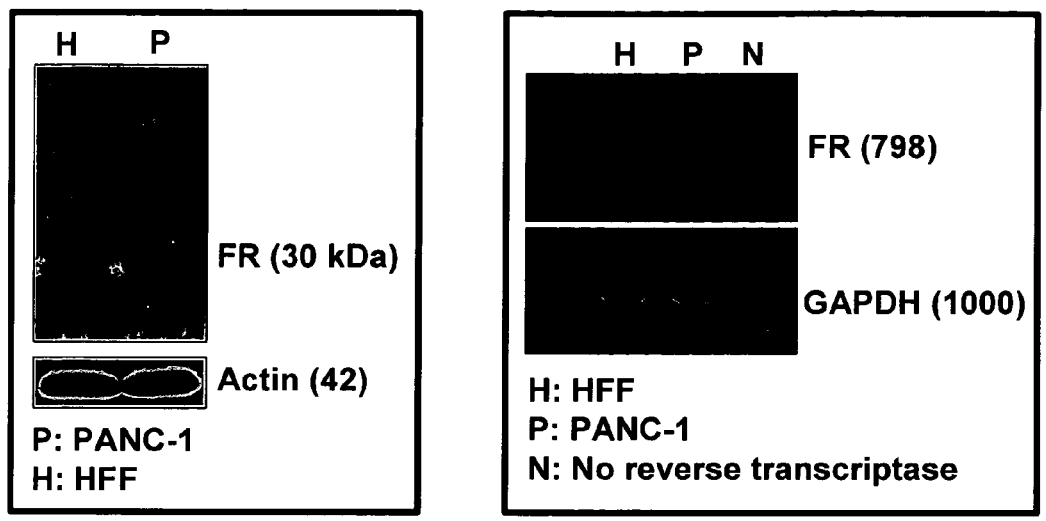
FIG. 9 shows Western blot (left) and RT-PCR (right) analysis that show that the α-folate receptor (FR) was overexpressed in PANC-1 cells, but not in HFF.
Figure 10:
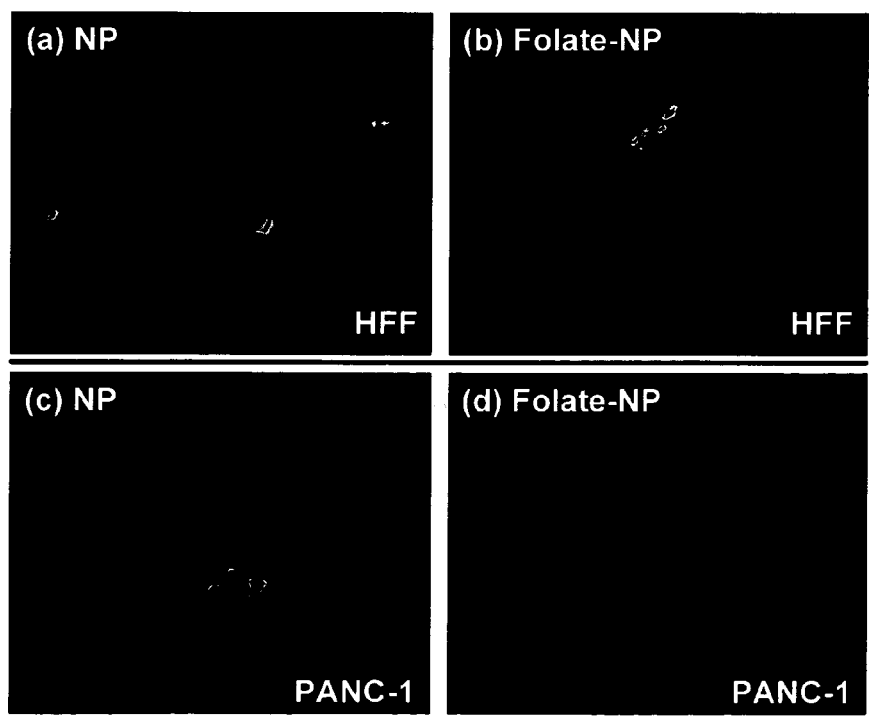
FIG. 10 shows fluorescence microscopy images showing the effect of folic acid modification on the NPs (green fluorescence). The cell nuclei were stained with DAPI (blue fluorescence) and the membranes were stained with WGA (red fluorescence). Top figures: HFF treated with (a) NPs and (b) folate-modified NPs. Bottom figures: PANC-1 treated with (c) NPs and (d) folate-modified NPs. Increased uptake of the folate-modified NPs was observed with the PANC-1 cells (overexpressed folate receptor), but not with the HFF.

The effect of folic acid modification on the cellular uptake of NPs was studied with the cancer cells PANC-1 and the human foreskin fibroblasts HFF. Western blot and reverse transcription polymerase chain reaction (RT-PCR) confirmed the overexpression of α-folate receptor on PANC-1 cells at both protein and mRNA level, but not on the HFF (FIG. 9). Although the cellular uptake of NPs was observed with both cell lines, folate modification on the NPs increased the particle uptake more than two-fold by the PANC-1, but not by the HFF (FIG. 10). These results corroborated the overexpression of folate receptor on PANC-1 cells, which may facilitate the recognition of the folate-modified NPs and increase the uptake through folate receptor-mediated endocytosis (Lee, R. J.; Low, P. S. Delivery of Liposomes into Cultured KB Cells via Folate Receptor-Mediated Endocytosis. *J. Biol. Chem.* 1994, 269, 3198-3204; Soppimath, K. S.; Liu, L. H.; Seow, W. Y.; Liu, S. Q.; Powell, R.; Chan, P.; Yang, Y. Y. Multifunctional Core/Shell Nanoparticles Self-Assembled from pH-Induced Thermosensitive Polymers for Targeted Intracellular Anticancer Drug Delivery. *Adv. Funct. Mater.* 2007, 17, 355-362).

Figure 11:
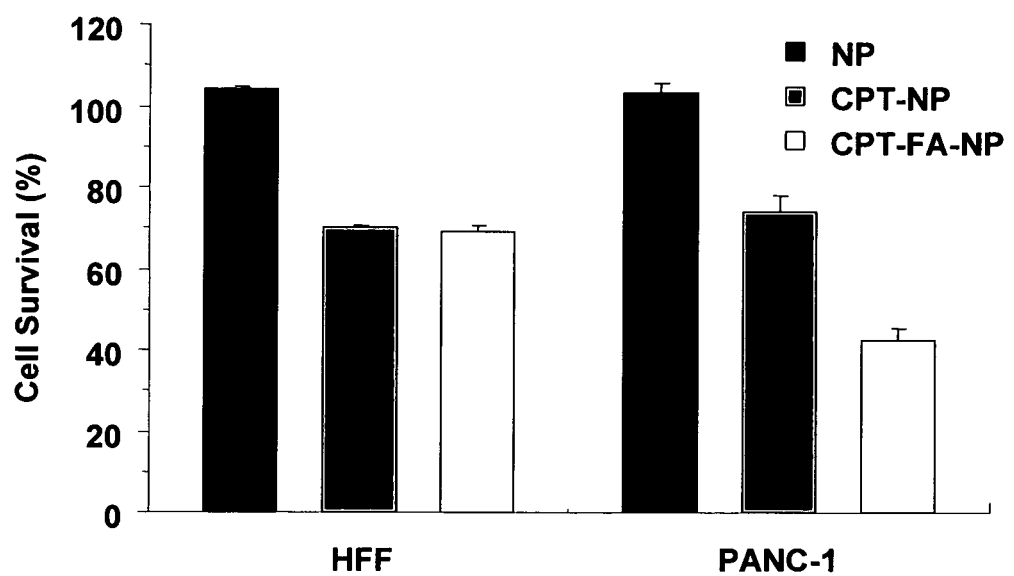
FIG. 11 shows cell growth inhibition assay of the folate-modified materials. The cells were treated for 24 h with nanoparticles only (NP), camptothecin-loaded nanoparticles (CPT-NP), or camptothecin-loaded nanoparticles modified with folic acid (CPT-FA-NP). The enhanced uptake of NPs by PANC-1 cells through folate modification led to an increase in the delivery of camptothecin. This effect was not observed on HFF, which do not overexpress folate receptors. The concentration of the NPs used was 20 μg/mL.

Folic acid modification to the CPT-loaded NPs can selectively increase the delivery of drugs to the cells that overexpress α-folate receptor. Because the NPs can enter both PANC-1 and HFF, the cytotoxicity of the CPT-loaded NPs was observed for both cell lines. However, there was a considerable increase in the cytotoxicity of folate-modifed CPT-loaded NPs to PANC-1 cells (FIG. 11), which correlated with the aforementioned enhanced particle uptake. More importantly, the cytotoxicity between the folate-modified and the unmodified CPT-loaded NPs was similar for the HFF since these cells do not overexpress the receptors. The result showed that folic acid modification to the NPs can increase the particle uptake and deliver more drugs to the cancer cells but not to the noncancerous fibroblasts.

Methods

Synthesis of Iron Oxide Nanocrystals.

The iron oxide nanocrystals (NCs) were synthesized by the thermal decomposition of iron-oleate complexes in a solution of oleic acid surfactants and octadecene solvent. 2.2 g iron (III) chloride hexahydrate (Sigma, 98%) and 7.4 g sodium oleate (TCI, 95%) were first dissolved in a mixture of 16.3 mL absolute ethanol and 12.2 mL water and mixed with 28.5 mL hexane. The solution was refluxed for 4 h. The mixture was then washed with water several times in a separatory funnel and the hexane was removed from the mixture by using rotary evaporation. The synthesized iron-oleate complex was then dried under vacuum overnight. 1 g of the iron-oleate complex was dissolved in a solution of 177.3 μL oleic acid (Aldrich, 90%) and 7.1 mL octadecene (Aldrich, 90%). The mixture was placed under vacuum and heated at 80° C. for 30 min. It was then stirred vigorously under nitrogen flow and heated to 320° C. at a rate of 3° C./minute and kept at that temperature for 1 h. After the mixture has cooled to room temperature, 5 mL hexane was added and the NCs were precipitated by adding an excess of ethanol. The NCs were separated from the solution by centrifugation. The NCs were then washed twice in a solution of 1:3 hexane-ethanol and dried under vacuum.

Mesoporous Silica Formation.

The dried oleate-capped iron oxide NCs were dissolved in chloroform. 2 mL (10-20 mg/mL) of the NCs solution was mixed with 0.4 g cetyltrimethylammonium bromide (CTAB, Aldrich, 95%) and 20 mL water. The mixture was then sonicated and stirred vigorously, and the chloroform solvent was boiled off from the solution. The aqueous CTAB-iron oxide NCs solution was filtered through a 0.44 μm syringe filter to remove any large aggregates or contaminants. 1 mg of fluorescein isothiocyanate (FITC, Sigma, 90%) was dissolved in 545 μL absolute ethanol and mixed with 2.2 μL aminopropyltriethoxysilane (APTS, Aldrich, 99%) for 2 h. 5 mL of the aqueous CTAB-stabilized NCs solution was added into a solution of 43 mL distilled water and 350 μL sodium hydroxide (2 M) and heated to 80° C. For higher concentration of iron oxide materials, the solution may need to be heated at lower temperature (65-70° C.) in order to avoid the coalescence of the mesoporous silica in forming large clumps of materials. After the temperature had stabilized, 0.6 mL of the ethanolic FITC-APTS solution was mixed with 0.5 mL tetraethylorthosilicate and added slowly into the aqueous solution containing the CTAB-stabilized NCs. After 15 min of stirring, 127 μL 3-(trihydroxysilyl)propyl methylphosphonate (Aldrich, 42%) was added into the mixture and the solution was stirred for another 2 h. The synthesized materials were centrifuged and washed with methanol. The CTAB surfactants were removed from the mesopores by dispersing the as-synthesized materials in a solution of 160 mg ammonium nitrate (Fisher) and 60 mL 95% ethanol, and heating the mixture at 60° C. for 15 min. The materials were then centrifuged and washed with ethanol.

Gold-Mesoporous Silica.

Gold NCs were synthesized by following the Brust method. 180 mg gold (III) chloride trihydrate (Aldrich, 99.9%) was dissolved in 15.3 mL water and mixed with 40.6 mL toluene solution containing 1.1 g tetraoctylammonium bromide (Aldrich, 98%). The solution was stirred vigorously for 30 min before adding 102.3 μL dodecanethiol (Aldrich, 98%). 12.7 mL aqueous solution of 192.1 mg sodium borohydride (Alfa Aesar, 97%) was then added slowly to the mixture. After further stirring for 3 h, the aqueous layer was removed using a separatory funnel and the toluene was removed using rotary evaporation. The solids were dissolved in a minimal amount of toluene, precipitated with absolute ethanol, and collected by centrifugation. After repeating the process two more times, the solids were dried under vacuum.

To synthesize the gold-mesoporous silica NPs, similar procedures were used as to make the iron oxide-mesoporous silica NPs.

Folic Acid Modification.

To attach folic acid to the iron oxide-mesoporous silica NPs, 20 mg of the materials (after removing the CTAB using the ion-exchange method) were washed with dimethyl sulfoxide (DMSO) and resuspended in DMSO. In a flask, 0.1 mg folic acid (Sigma, 98%) and 0.05 μL APTS were mixed in 1 mL DMSO. 0.03 mg N-hydroxysuccinimide (Aldrich, 98%) and 0.05 mg 1-(3-dimethylaminopropyl)-3-ethylcarbodiimide hydrochloride (Alfa Aesar, 98%) was then added into the mixture and stirred for 2 h. In a separate flask containing 4 mL toluene and the NPs-DMSO suspension, the folate-APTS solution was added and the mixture was stirred for 20 h at room temperature. The materials were recovered by centrifugation, washed twice with toluene, and dried under vacuum.

Drug Loading.

The modified materials were loaded with either camptothecin (CPT) (Sigma, 95%) or paclitaxel (TXL) (Sigma)

by incubating 10 mg of the materials in a solution of 1 mg drugs and 0.25 mL DMSO for 4 h. After centrifuging the drug-loaded NPs from the suspension and removing the supernatant completely, the materials were then dried under vacuum. The drug-loaded NPs were then washed and sonicated with water before resuspending them in aqueous solution.

In order to determine the amount of drugs that were inside the NPs, the aqueous drug-loaded NPs suspension were incubated at 4° C. for 6 h before centrifugation to show that the drugs were not being slowly released from the mesopores. The resulting supernatant was mixed with the previous supernatant solution from the washing process and measured using UV/Vis absorption spectroscopy. The drug-loaded NPs pellet were resuspended and sonicated in DMSO (or methanol for TXL-loaded NPs) and collected by centrifugation. The process was repeated two more times (~15 min total time) to ensure that the drugs were completely removed from the pores. The DMSO (or methanol) supernatants were then measured using UV/Vis absorption.

Cell Culture.

Human cancer cell lines PANC-1 and BxPC3 were obtained from the American Type Culture Collection and human foreskin fibroblasts (HFF) were a generous gift from Dr. Peter Bradley at UCLA. The cells were maintained in Dulbecco's modified Eagle's medium (DMEM, GIBCO) supplemented with 10% fetal calf serum, 2% L-glutamine, 1% penicillin, and 1% streptomycin stock solutions. The media were changed every three days, and the cells were passaged by trypsinization before confluence.

Fluorescence Microscopy.

The cellular uptake of the NPs was confirmed by fluorescence microscopy. The cells were incubated in an 8-well cell culture chamber with the NPs and then washed with DMEM and PBS to wash off the NPs that did not enter the cells. The cells were then stained with DAPI solution and/or WGA-Alexa Fluor 594 before monitoring using the fluorescence microscope.

Cell Viability Assay.

The cytotoxicity assay was performed by using a cell-counting kit from Dojindo Molecular Technologies, Inc. Cells were seeded in 96-well plates (5000 cells per well) and incubated in fresh culture medium at 37° C. in a 5% $CO_2$/95% air atmosphere for 24 h. The cells were then washed with PBS and the medium was replaced with a fresh medium containing the NPs or the drug-loaded NPs. After 24 h, the cells were washed with PBS and incubated in fresh medium for an additional 48 h. The cells were washed with PBS and incubated in DMEM with 10% WST-8 solution for another 2 h. The absorbance of each well was measured at 450 nm with a plate reader. Since the absorbance is proportional to the number of viable cells in the medium, the viable cell number was determined by using a previously prepared calibration curve (Dojindo Co.).

Western Blot Analysis.

Cell lysate was separated by gel electrophoresis on a polyacrylamide gel containing sodium dodecyl sulfate and then transferred to nitrocellulose membranes. The membranes were blocked with Tris-buffered saline (TBS) containing 5% (w/v) skimmed milk. After being washed with TBS containing 0.1% Tween 20 (Sigma), the membranes were incubated overnight at room temperature with α-folate receptor (F-15) antibody (Santa Cruz Biotechnology) diluted with TBS. After being washed, the membranes were incubated for 2 h at room temperature with the second antibody (Santa Cruz Biotechnology). Bands were detected with an ECL system (Amersham Pharmacia Biotech.)

Reverse Transcription Polymerase Chain Reaction (RT-PCR).

RT-PCR was performed using a platinum taq DNA polymerase high fidelity RT-PCR kit. The cells were harvested from culture dishes. RNA was extracted using TRIzol reagents (Invitrogen) and 1 μg RNA was reverse-transcribed. The resulting cDNAs were amplified by PCR reaction using primers for human folate receptor (forward: AACACAGCTGCTGCTCCTTCTAGT; reverse: AACAGGGCAGGGATTTCCAGGTAT). The PCR reaction was conducted at 40 cycles. Each cycle consisted of 30 s at 94° C., 30 s at 57° C., and 1 min at 72° C. The reaction products were electrophoresed in 1% TAB agarose gel. The gel was stained by ethidium bromide, and then photographed.

Magnetic Resonance (MR) Imaging.

The MR imaging experiments were performed on Siemens Avanto 1.5-T MR system. Extremity coil was used for the data acquisition and the pulse sequence used was T2-weighted Turbo Spin-Echo sequence with the following parameters: TR=4620 ms, slice thickness=3 mm, TE=98 ms, field of view=157×180 mm, number of acquisition=1. For the experiments to observe the MR contrast effect of the NPs within the cells, PANC-1 cells were incubated with either the iron oxide-mesoporous silica NPs or plain mesoporous silica NPs for 1 h and 4 h period, trypsinized, and then placed in 0.2 mL PCR tube. Each tube contained approximately $10^5$ cells.

Example 2

CPT and its derivatives are considered to be one of the most promising anticancer drugs of the 21st century (F. M. Muggia, I. Dimery, S. G. Arbuck, *Ann. N.Y. Acad. Sci.* 1996, 803, 213). Although studies have demonstrated their effectiveness against carcinomas of the stomach (D. A. Litvak, H. T. Papaconstantinou, K. O. Hwang, M. Kim, B. M. Evers, C. M. Townsend, *Surgery* 1999, 126, 223), colon (S. Takiguchi, T. Shimazoe, A. Kono, *Gan To Kagaku Ryoho* 1994, 21, 705), neck (D. Abigerges, G. G. Chabot, J. P. Armand, P. Herait, A. Gouyette, D. Gandia, *J. Clin. Oncol.* 1995, 13, 210) and bladder (T. E. Keane, R. E. El-Galley, C. Sun, J. A. Petros, D. Dillahey, A. Gomaa, S. D. Graham, Jr., W. P. McGuire, 3rd, *J. Urol.* 1998, 160, 252), as well as breast (K. D. Miller, S. E. Soule, L. G. Haney, P. Guiney, D. J. Murry, L. Lenaz, S. L. Sun, G. W. Sledge, *Invest. New Drugs* 2004, 22, 69), small-cell lung cancer (N. Masuda, M. Fukuoka, Y. Kusunoki, K. Matsui, N. Takifuji, S. Kudoh, S. Negoro, M. Nishioka, K. Nakagawa, M. Takada, *J. Clin. Oncol.* 1992, 10, 1225) and leukemia (R. P. Hertzberg, M. J. Caranfa, K. G. Holden, D. R. Jakas, G. Gallagher, M. R. Mattern, S. M. Mong, J. O. Bartus, R. K. Johnson, W. D. Kingsbury, *J. Med. Chem.* 1989, 32, 715) in vitro, clinical application of CPT in humans has not been achieved to date because its poor water solubility requires changes to their physicochemical characteristics. The need to formulate water soluble salts of CPT (i.e. alkaline solutions for intravenous injections) led to chemical modifications of the molecule with loss of antitumor activity and significant alterations in the toxicological profile of the drug (R. P. Hertzberg, M. J. Caranfa, K. G. Holden, D. R. Jakas, G. Gallagher, M. R. Mattern, S. M. Mong, J. O. Bartus, R. K. Johnson, W. D. Kingsbury, *J. Med. Chem.* 1989, 32, 715; D. O. Scott, D. S. Bindra, V. J. Stella, *Pharm. Res.* 1993, 10, 1451; A. Guiotto, M. Canevari, P. Orsolini, O. Lavanchy, C. Deuschel, N. Kaneda, A. Kurita, T. Matsuzaki, T. Yaegashi, S. Sawada, F. M. Veronese, *J. Med. Chem.* 2004, 47, 1280; H. Onishi, Y. Machida, *Curr. Drug Discovery Technol.* 2005, 2, 169). Although its derivatives such as irinotecan have produced good clinical results (C. Fuchs, E. P. Mitchell, P. M. Hoff, *Cancer Treat. Rev.* 2006, 32, 491), irinotecan was shown to have far lower cytotoxicity to cancer cells compared to CPT (10%), and CPT remains the most potent compound (K. S. Cunha, M. L. Reguly, U. Graf, H. H. Rodrigues de Andrade, *Mutagenesis* 2002, 17, 141).

Among a variety of drug delivery systems, mesoporous silica materials (C. T. L. Kresge, M. E.; Roth, W. J.; Vartuli, J. C.; Beck, J. S, *Nature* 1992, 359, 0028) have several attractive features for use in the delivery of water-insoluble drugs. These particles have large surface areas and porous interiors that can be used as reservoirs for storing hydrophobic drugs. The pore size and environment can be tailored to selectively store different molecules of interest (B. Munoz, A. Ramila, J. Perez-Pariente, I. Diaz, M. Vallet-Regi, *Chem. Mater.* 2003, 15, 500; Y. J. Han, G. D. Stucky, A. Butler, *J. Am. Chem. Soc.* 1999, 121, 9897), while the size and shape of the particles can be tuned to maximize cellular uptake. Unlike polymer-based nanoparticles, these robust inorganic materials can tolerate many organic solvents (A. Stein, B. J. Melde, R. C. Schroden, *Adv. Mater.* 2000, 12, 1403). Silica-based materials have successfully been used as drug delivery vectors (M. Arruebo, M. Galan, N. Navascues, C. Tellez, C. Marquina, M. R. Ibarra, J. Santamaria, *Chem. Mater.* 2006, 18, 1911; M. Arruebo, R. Fernandez-Pacheco, S. Irusta, J. Arbiol, M. R. Ibarra, J. Santamaria, *Nanotechnology* 2006, 17, 4057), gene transfection reagents (D. R. Radu, C. Y. Lai, K. Jeftinija, E. W. Rowe, S. Jeftinija, V. S. Y. Lin, *J. Am. Chem. Soc.* 2004, 126, 13216.), cell markers (Y. S. Lin, C. P. Tsai, H. Y. Huang, C. T. Kuo, Y. Hung, D. M. Huang, Y. C. Chen, C. Y. Mou, *Chem. Mater.* 2005, 17, 4570), and carriers of molecules (C. Y. Lai, B. G. Trewyn, D. M. Jeftinija, K. Jeftinija, S. Xu, S. Jeftinija, V. S. Y. Lin, *J. Am. Chem. Soc.* 2003, 125, 4451). Here we describe the preparation of fluorescent mesoporous silica nanoparticles according to an embodiment of the current invention that are highly stable in aqueous solution and their use for the delivery of the hydrophobic anticancer drug CPT.

Figures 12A, 12B:
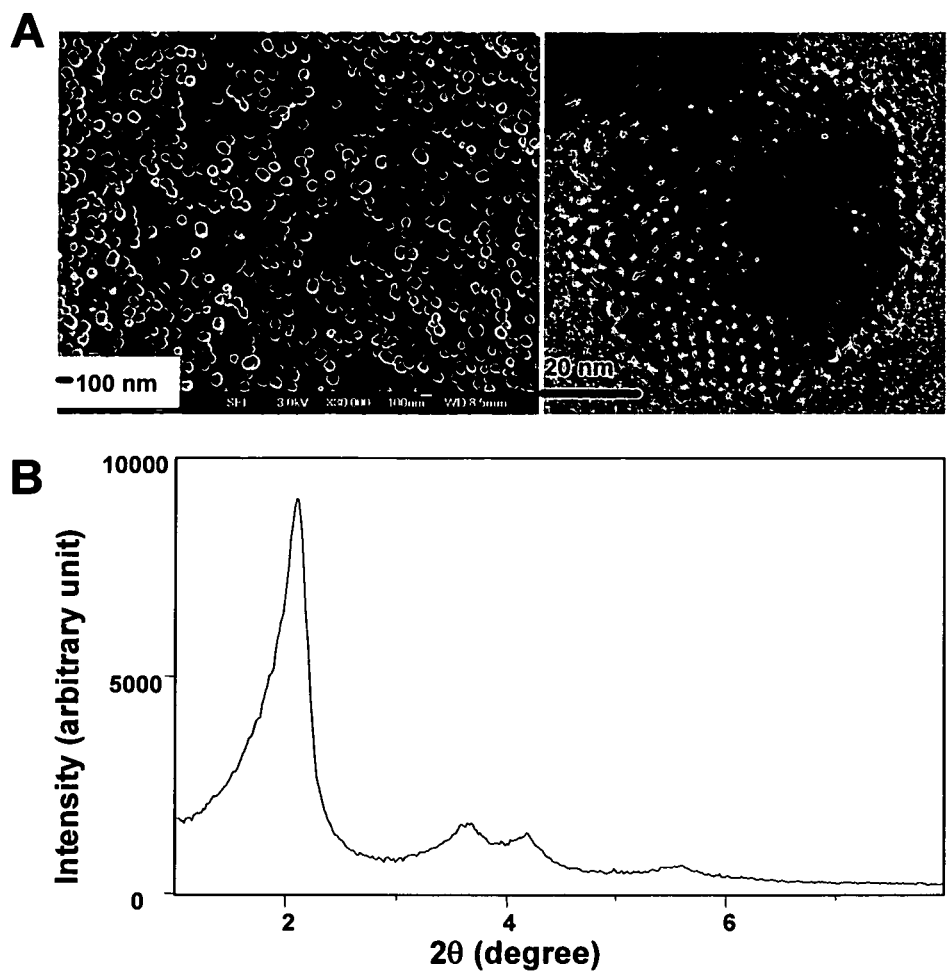
FIGS. 12A and 12B show characterization of the FMSN.

The FMSN were prepared using a base-catalyzed sol-gel process at high temperature using a modification of published procedures (Y. S. Lin, C. P. Tsai, H. Y. Huang, C. T. Kuo, Y. Hung, D. M. Huang, Y. C. Chen, C. Y. Mou, *Chem. Mater.* 2005, 17, 4570; S. Huh, J. W. Wiench, J. C. Yoo, M. Pruski, V. S. Y. Lin, *Chem. Mater.* 2003, 15, 4247; I. Slowing, B. G. Trewyn, V. S. Y. Lin, *J. Am. Chem. Soc.* 2006, 128, 14792). In a typical synthesis, fluorescein isothiocyanate was first reacted with 3-aminopropyl-triethoxysilane (APTS) in ethanol. The mixture was then added along with tetraethyl orthosilicate to cetyltrimethylammonium bromide solution at 80° C. The surfactants were removed from the pores by refluxing the nanoparticles in acidic methanol, which was confirmed by Fourier Transform Infrared Spectroscopy (FTIR). Electron microscope and X-ray diffraction (XRD) analysis showed that the particle shape and hexagonal arrays of the pores in the FMSN remained intact after the surfactant removal process (FIGS. 12A and 12B). The nanoparticles were roughly spherical in shape and smaller than 130 nm in diameter. An average pore diameter of around 2 nm was observed using transmission electron microscope and an interplanar spacing $d_{100} \approx 4$ nm was calculated from the XRD pattern.

It is necessary that the FMSN remain dispersed and do not aggregate in buffer solution for efficient cellular uptake of the particles. The observed aggregation is caused by the interparticle hydrogen bonding interactions between the amine groups (from the unreacted APTS) and the silanols (FIG. 13A). By modifying only the surfaces of the FMSN with trihydroxysilyl-propyl methylphosphonate (THMP) after the particle formation (R. P. Bagwe, L. R. Hilliard, W. Tan, *Langmuir* 2006, 22, 4357), we reduced the aggregation and increased the stability of the particles in aqueous solution (FIG. 13B).

Figures 14A, 14B, 14C, 14D:
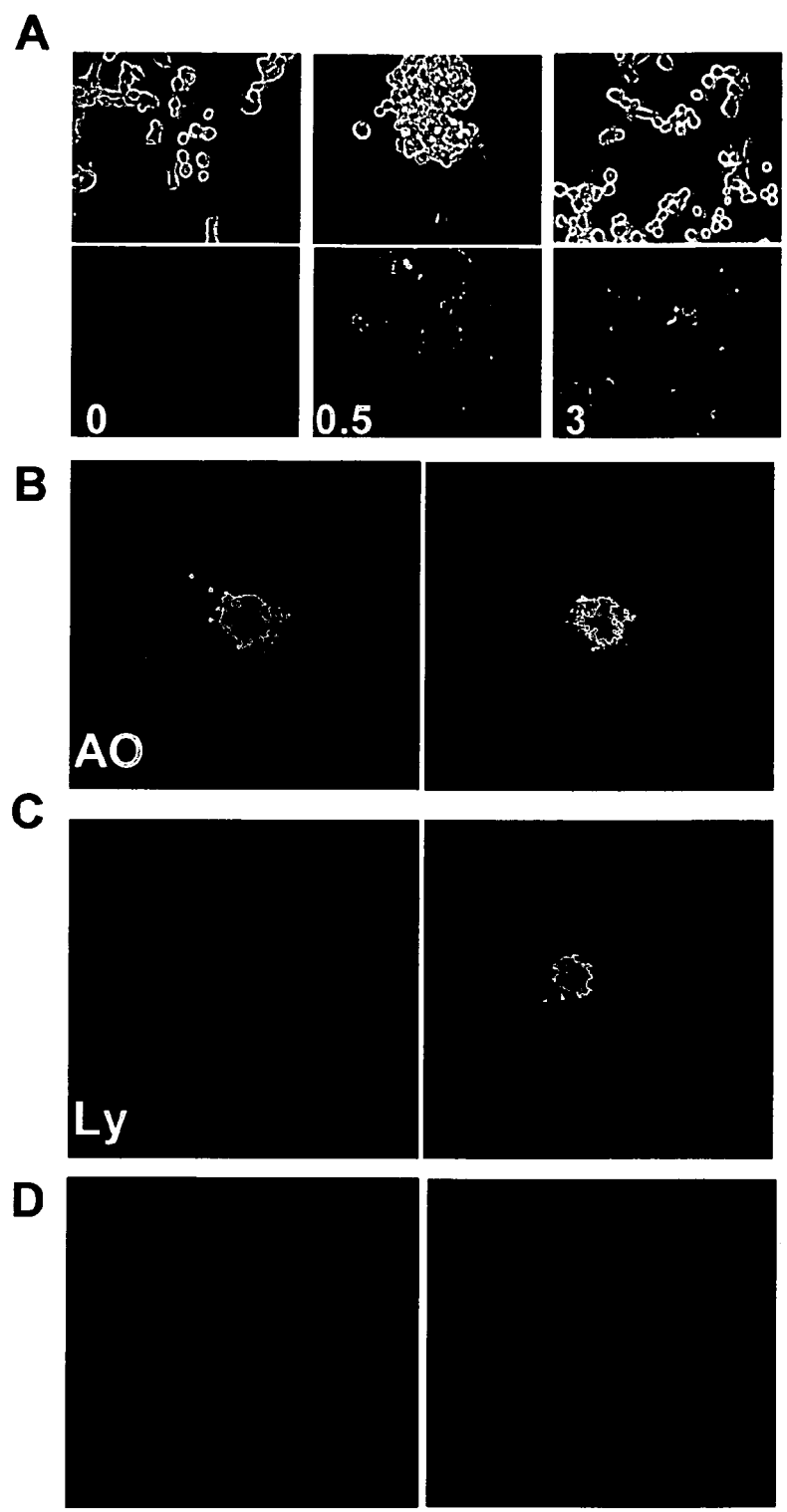
FIGS. 14A-14D show uptake of the nanoparticles by cancer cells according to an embodiment of the current invention.

The uptake of the nanoparticles by various cancer cell lines was observed using fluorescence and confocal microscopies. Cancer cells were incubated with FMSN and then washed with phosphate buffered saline solution (PBS) to remove the nanoparticles that were not taken up by cells. The emission of the nanoparticles, which were derivatized with fluorescein molecules, was monitored by fluorescence microscope (FIG. 14A). To further specify the intracellular location of the nanoparticles, Acridine Orange (AO) and lysoSensor green DND-189 were used to stain the cells that were incubated with the FMSN. AO specifically stains acidic organelles such as lysosomes and endosomes to red, but stains other cellular regions to green (P. G. Canonico, J. W. C. Bird, *J. Cell Biol.* 1969, 43, 367), while lysoSensor specifically stains lysosomes to green. The fluorescence of the nanoparticles overlapped mostly with the red fluorescence of AO (FIG. 14B) as well as with the green fluorescence of lysoSensor (FIG. 14C). This result suggested that the FMSN were mainly taken into the acidic organelles.

Figure 15:
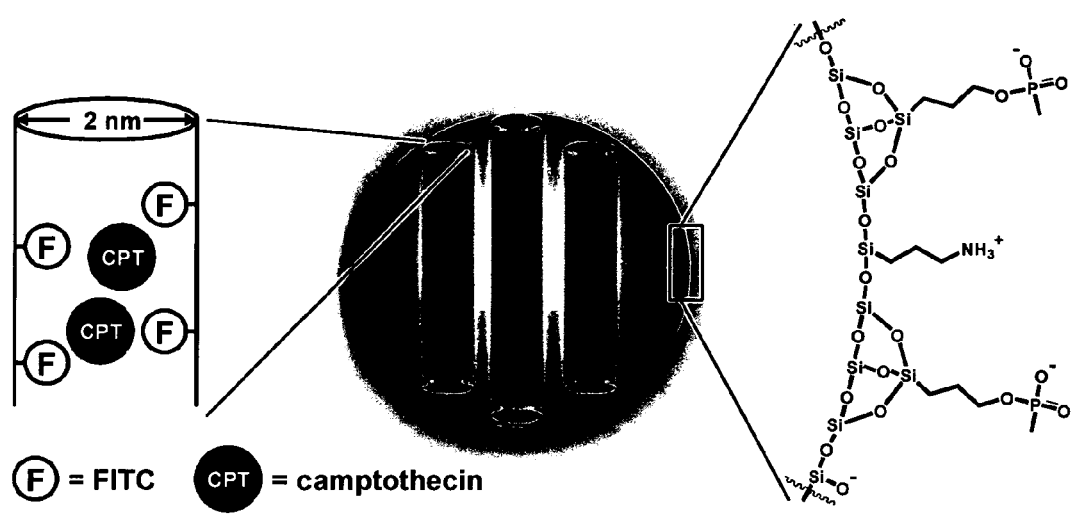
FIG. 15 is a schematic representation of the CPT-loaded FMSN (~130 nm diameter). The 2 nm diameter pores (not drawn to scale) of the nanoparticles were derivatized with FITC and filled with CPT drug molecules, and the FMSN surface was modified with THMP.

The nanoparticles were loaded with drug molecules by soaking them in a DMSO solution of CPT overnight. The size of CPT molecule is approximately 1.3 nm×0.6 nm as to fit into the pores of FMSN. After the organic solvent was removed using centrifugation and high vacuum, the loaded nanoparticles were sonicated and washed twice with PBS to ensure that any weakly adsorbed drugs on the surface were removed (FIG. 15). The release profile in solution showed only minimal release of CPT when the CPT-loaded nanoparticles were soaked in aqueous solution. Absorption measurements by UV/Vis spectroscopy determined that 50 mg of the FMSN could store approximately 80 nmol of CPT.

A homogeneous suspension of the CPT-loaded FMSN in PBS was added to PANC-1 cells to determine if the nanoparticles were able to transport the hydrophobic CPT into cancer cells. As a control experiment, a suspension of CPT in PBS with the same concentration was added to the cells. Because CPT emits a strong blue fluorescence under UV excitation and its excitation wavelength is different from that of the FMSN, we used fluorescence microscope to monitor the distribution of CPT in cancer cells. The cells that were treated with CPT-loaded FMSN showed strong blue fluorescence (FIG. 14D right) after 3 hours incubation, while those that were treated with suspension of CPT in PBS remained nonfluorescent (FIG. 14D left). This observation indicated that the FMSN were able to transport and deliver CPT inside the cancer cells.

Figure 16:
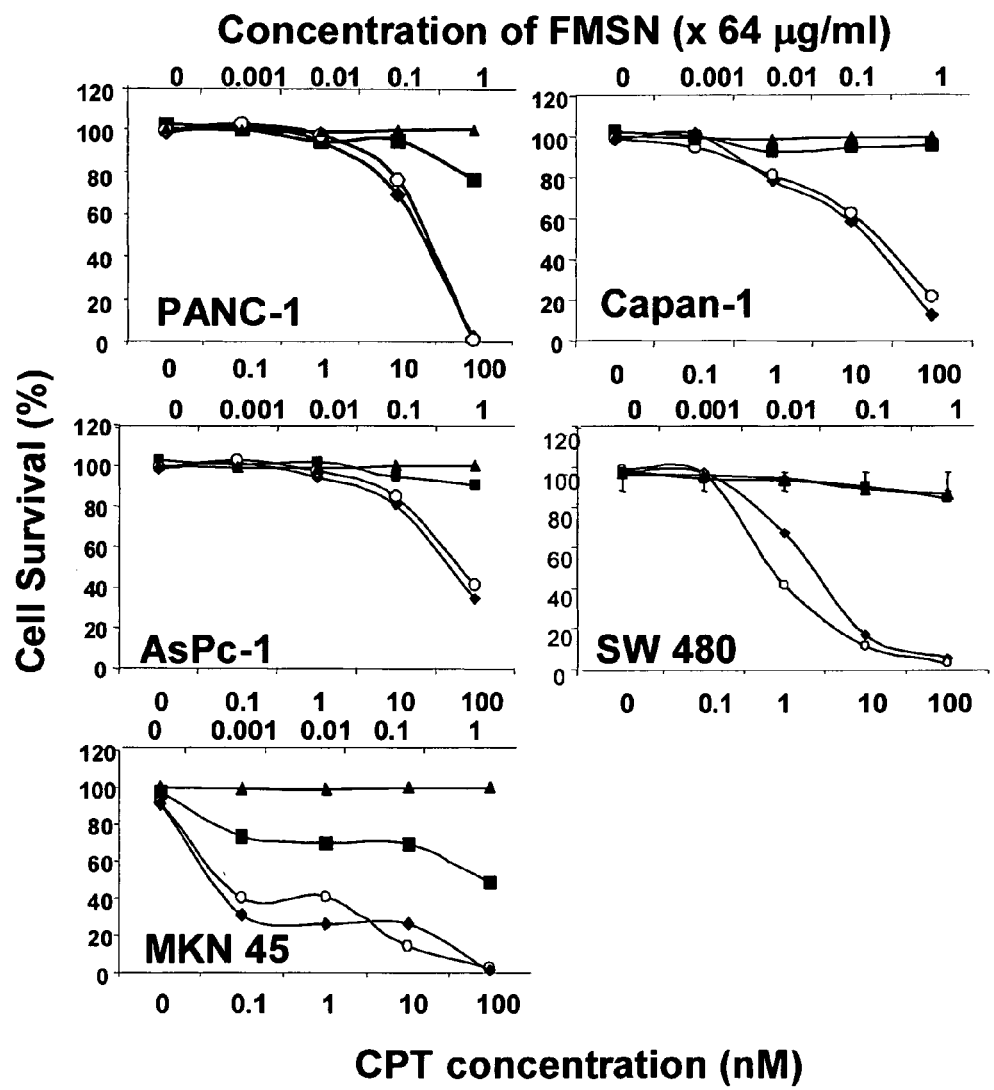
FIG. 16 shows cell growth inhibition assay. ▲: nonloaded FMSN in PBS; ■: CPT in PBS; ○: CPT in DMSO; ♦: CPT-loaded FMSN in PBS. The concentration of FMSN is shown on top of each figure, while the concentration of CPT in DMSO, in PBS, or loaded in FMSN, is shown under each figure.

Delivering CPT into cancer cells led to growth inhibition and cell death. This cytotoxic effect of CPT-loaded FMSN was tested on several cancer cell lines. As shown in FIG. 16, nonloaded FMSN alone were not toxic to any of the cells tested, indicating good biocompatibility of the nanoparticles. However, growth inhibition of different human cancer cells was observed with the cells treated with either the suspension of CPT-loaded FMSN in PBS or solution of CPT in DMSO. Survival of three pancreatic cancer cell lines (PANC-1, Capan-1 and AsPc-1), a colon cancer cell line (SW480), and a stomach cancer cell line (MKN-45) (FIG. 16) was decreased by CPT-loaded FMSN. The cytotoxic efficacy of the CPT-loaded FMSN was very similar to that of CPT dissolved in DMSO. In contrast, CPT suspended in PBS did not show any cytotoxicity to cancer cells even at high concentrations. This is consistent with our observation that CPT suspended in PBS was not taken up by cells due to its insolubility while CPT loaded in FMSN was quickly taken up (FIG. 14D). Thus, FMSN effectively delivered the hydrophobic CPT into cancer cells with minimal leakage in the buffer solution and culture medium.

Figures 17A, 17B, 17C, 17D, 17E, 17F:
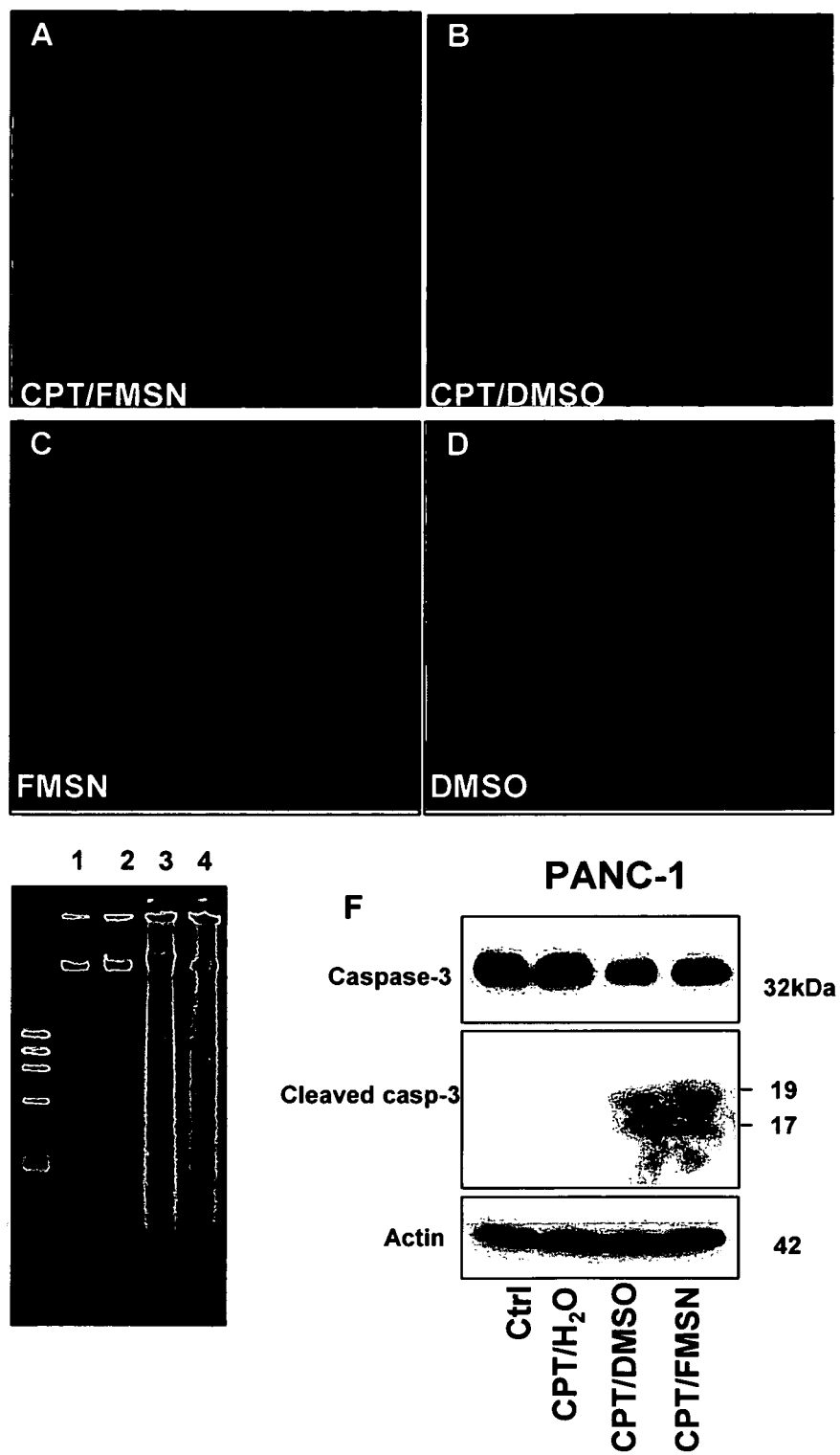
FIGS. 17A-17F show apoptosis induced by CPT-loaded FMSN. PANC-1 cells were incubated for 24 hours with A) CPT-loaded FMSN, B) CPT in DMSO, C) CPT in PBS, or D) 10% DMSO, and then stained with propidium iodide/Hoechst 33342. E) DNA fragmentation assay. PANC-1 cells were treated with (1) PBS, (2) CPT in PBS, (3) CPT in DMSO, or (4) CPT-loaded FMSN in PBS. F) The western blot result. Ctrl: control; CPT/H2O: CPT in water; CPT/DMSO: CPT in DMSO; CPT/FMSN: CPT-loaded FMSN. The first antibodies used are caspase-3 and cleaved caspase-3.

To check if the cell death induced by the CPT-loaded FMSN was due to the cytotoxicity of the drug, the mechanism of cell death was investigated. After PANC-1 cells were incubated with: (1) CPT-loaded FMSN suspended in PBS, (2) CPT dissolved in DMSO, or (3) nonloaded FMSN suspended in PBS as the control for 24 hours, they were double stained with propidium iodide and Hoechst 33342 (J. Hasegawa, S. Kamada, W. Kamiike, S. Shimizu, T. Imazu, H. Matsuda, Y. Tsujimoto, *Cancer Res.* 1996, 56, 1713). Nuclear fragmentation and chromatin condensation were observed in most of the cells treated with CPT-loaded FMSN (FIG. 17A), similar to the cells treated with CPT in DMSO (FIG. 17B), while the cells treated with 10% DMSO that induced necrosis were stained with propidium iodide (red) (FIG. 17D). These results indicate that the CPT-loaded FMSN induced apoptotic cell death. Further confirmation of apoptosis came from the detection of DNA fragmentation (FIG. 17E) and Western blot result of cleaved caspase-3 in the cells treated with CPT-loaded FMSN (FIG. 17F).

In summary, we have successfully loaded hydrophobic anticancer drugs into mesoporous nanoparticles and delivered them into human cancer cells to induce apoptosis according to an embodiment of the current invention. A similar anticancer effect was observed between the CPT in DMSO and CPT-loaded FMSN in PBS, suggesting minimal drug leakage in the buffer solution and cell medium. CPT remained inside the nanoparticles and released only in the hydrophobic regions of the cell compartments to exert the apoptotic effect. At present, about 40% of small-molecule drugs in the pipeline of pharmaceutical companies has low water solubility and therefore cannot be administered via the preferred route or in some cases, at all (V. Wagner, A. Dullaart, A. K. Bock, A. Zweck, *Nat. Biotechnol.* 2006, 24, 1211). Our results with CPT suggest that the mesoporous silica nanoparticles may offer a solution to this problem in drug development. Mesoporous nanoparticles also offer the possibility to accomplish controlled release of anticancer drugs. The pores in the nanoparticles could be closed by constructing an appropriate cap structure. The ability to control the release of anticancer drugs provides mesoporous silica nanoparticles with advantages over other drug delivery systems such as pegylated liposomal particles or the use of albumin based nanoparticles.

Experimental

Synthesis of Nanoparticles and Loading of CPT:

All chemicals for the synthesis of the nanoparticles were purchased from Sigma-Aldrich. The fluorescent mesoporous silica nanoparticles (FMSN) were synthesized by first dissolving 5.5 mg fluorescein isothiocyanate (FITC) in 3 mL absolute ethanol before adding 12 µL aminopropyltriethoxysilane (APTS). In another container, 0.5 g cetyltrimethylammonium bromide (CTAB) was dissolved in a solution of 240 mL distilled water and 1.75 mL sodium hydroxide (2 M) that was heated to 80° C. and stirred vigorously. The solution of FITC-APTS was stirred under inert atmosphere for 2 hours before adding 2.5 mL tetraethylorthosilicate (TEOS). Once the temperature of the CTAB solution had stabilized, the ethanol solution containing TEOS and FITC-APTS was added. After 15 minutes, 0.63 mL of 3-trihydroxysilylpropyl methylphosphonate was slowly added to the mixture. After 2 hours, the solution was cooled to room temperature and the particles were filtered and washed with methanol using fritted funnel. The particles were allowed to dry at room temperature overnight. To remove the surfactants from the pores of the particles, 850 mg of particles were dissolved in a solution of 90 mL methanol and 5 mL hydrochloric acid (12.1 M) and refluxed for 24 hours. The particles were then filtered and washed thoroughly to remove the surfactants and unbound FITC.

To load drug molecules into the pores of the particles, FMSN was soaked in a concentrated solution containing the drugs. Typically, 50 mg of the FMSN was stirred in a solution containing 5 mg camptothecin (CPT) and 3 mL DMSO. After 24 hours, the mixture was centrifuged and the supernatant was removed. Using UVNis spectroscopy, the absorption measurements of the original solution and the supernatant were compared to determine the amount of CPT that was loaded inside the FMSN. The drug-loaded FMSN was dried under vacuum to remove trace DMSO, and then sonicated and washed twice with phosphate buffered saline pH 7.4 solution (PBS) to remove CPT that were adsorbed on the surface and not inside the pores.

Cell Culture:

Human cancer cell lines, PANC-1, AsPC-1, Capan-1 (pancreatic), MKN45 (gastric), and SW480 (colon) were obtained from the American Type Culture Collection and were maintained in Dulbecco's modified Eagle's medium (DMEM) (GIBCO) or RPMI-1640 (Cellgro) supplemented with 10% fetal calf serum (Sigma), 2% L-glutamine, 1% penicillin, and 1% streptomycin stock solutions. The media were changed every 3 days, and the cells were passaged by trypsinization before confluence.

Fluorescence and Confocal Microscopies:

The fluorescence of the nanoparticles at 470 nm excitation wavelength was used to confirm the cellular uptake of FMSN. PANC-1, Capan-1, and AsPc-1 cancer cells were incubated with FMSN for various time periods and then washed with medium and PBS to wash off the nanoparticles that did not enter the cells. The cells were then monitored by fluorescence microscope with an excitation wavelength at 470 nm. To examine the location of FMSN within the cells, Acridine Orange (AO) (Sigma) and lysoSensor green DND-189 (Invitrogen) were used to monitor lysosomes and endosomes. Cells were cultured overnight on a Lab-Tek chamber slide system (Nalge Nunc International). After the cells were incubated with FMSN for 3 hours, they were washed with PBS and examined with confocal microscope ($\lambda$ex=470 nm) (Carl Zeiss LSM 310 Laser Scanning Confocal microscope). The same cells were then incubated with 6 µM AO or 1 µM of lysoSensor green DND-189 for 1 hour in DMEM without phenol red, washed with PBS, and examined by confocal microscope again ($\lambda$ex=488 nm and 440 nm). The emission of the FMSN was passed through a 560-nm short-pass dichroic mirror. The green emission was passed through a 530-nm bandpass filter and the red emission was passed through a 600-nm longpass filter; both emissions were simultaneously collected using two photomultiplier tubes. CPT exhibits intense blue fluorescence under UV light. This property allows the use of fluorescence to study the distribution of CPT inside the cells. PANC-1 cells were incubated with CPT-loaded FMSN or CPT suspended in PBS (100 nM) for 3 hours, washed with PBS 3 times, and then examined by fluorescece microscope under UV.

Cell Death Assay:

The cytotoxicity assay was performed using a cell counting kit from Dojindo Molecular Technologies, Inc. Cancer cells were seeded in 96-well plates (5000 cells/well) and incubated in fresh culture medium at 37° C. in a 5% $CO_2$/95% air atmosphere for 24 hours. The cells were then washed with PBS and the medium was changed to a fresh medium along with the CPT in DMSO, CPT-loaded FMSN in PBS, FMSN or CPT suspended in PBS at the indicated concentrations. After 24 hours, the cells were washed with PBS to remove the CPT and FMSN that were not taken up by the cells, and incubated in fresh medium for an additional 48 hours. The cells were then washed with PBS and incubated in DMEM with 10% WST-8 solution for another 2 hours. The absorbance of each well was measured at 450 nm with a plate reader. Since the absorbance is proportional to the number of viable cells in the medium, the viable cell number was determined using a previously prepared calibration curve (Dojindo Co.).

Apoptosis Assay:

Cell death was also examined using the propidium iodide and Hoechst 33342 double-staining method. The cells were stained with propidium iodide/Hoechst 33342 (1:1) for 5 minutes and then examined using fluorescence microscope. DNA fragmentation assay was also performed. PANC-1 cells were treated for 24 hours with: (1) 100 nM CPT in PBS, (2) 100 nM CPT loaded in FMSN (suspended in PBS), or (3) 64 µg/ml nonloaded FMSN in PBS, then washed twice with ice-cold PBS and collected by trypsinization. The cell pellets were resuspended in 500 µl of Tris-EDTA buffer (20 mM Tris-HCl [pH 8.0], 20 mM EDTA) containing 0.1% SDS and proteinase K (0.5 mg/ml) at 50° C. for 2 hours and then treated with RNase A (0.02 mg/ml) for 30 minutes at 37° C. DNA was extracted using phenol/chloroform and ethanol precipitation and was dissolved in distilled water, separated on a 2% agarose gel, and stained with ethidium bromide.

Western Blot Analysis:

Proteins were separated by gel electrophoresis on a polyacrylamide gel containing sodium dodecyl sulfate (SDS), and then transferred to nitrocellulose membranes. The membranes were blocked with tris buffer saline (TBS) containing 5% (W/V) skim milk. After washing with TBS containing 0.1% Tween 20 (Sigma), the membranes were incubated overnight at room temperature with caspase-3 antibody (BD Science) and cleaved caspase-3 antibody (Cellsignaling) diluted with TBS. After washing, the membranes were incubated for 2 hours at room temperature with the second antibody (Santa Cruz Biotechnology, CA). Bands were detected with an ECL system (Amersham Pharmacia Biotech K.K., UK).

Statistical Analysis:

All results are expressed as means±SD. Statistical comparisons were made using Student's t-test after analysis of variance. The results were considered to be significantly different at P value<0.05.

Example 3

In this example, we first addressed the mechanism of uptake of fluorescent mesoporous silica nanoparticles (FMSN) into cancer cells. Different incubation temperatures as well as various chemicals were used to gain insight into the uptake mechanism. We also examined whether a hydrophobic anticancer drug paclitaxel can be delivered into cancer cells by utilizing FMSN as a drug nanocarrier. Here, we report that FMSN can be taken up by human cancer cells through energy-dependent endocytosis mechanism, and that FMSN can be used as a delivery vehicle for paclitaxel.

Experimental

Synthesis of Nanoparticles.

All chemicals used for the synthesis of the nanoparticles were purchased from Sigma-Aldrich and used without further purification. In a round-bottom flask, 12 µL aminopropyltriethoxysilane (APTS) was added to a solution of 5.5 mg fluorescein isothiocyanate (FITC) and 3 mL absolute ethanol and stirred under inert atmosphere. In another container, 0.5 g cetyltrimethylammonium bromide (CTAB) was dissolved in a solution of 240 mL distilled water and 1.75 mL sodium hydroxide (2 M) and stirred vigorously at 80° C. The solution of FITC-APTS was stirred for 2 h before adding 2.5 mL tetraethylorthosilicate (TEOS). Once the temperature of the CTAB solution had stabilized, the ethanol solution containing TEOS and FITC-APTS was added. After 15 min, 0.63 mL of 3-trihydroxysilylpropyl methylphosphonate was added to the mixture. 2 h later, the solution was cooled to room temperature and the particles were filtered and washed with methanol. The particles were dried at room temperature overnight. To remove the surfactants from the pores of the particles, 850 mg of particles were dispersed in a solution of 90 mL methanol and 5 mL hydrochloric acid (12.1 M) and refluxed for 24 h. The particles were then filtered, washed thoroughly with methanol, and dried at room temperature.

Materials Characterization.

FMSN were analyzed using scanning electron microscopy (SEM) and transmission electron microscopy (TEM). For the TEM analysis, a drop of diluted FMSN solution was deposited onto copper grid and dried at room temperature. The images were collected using JEOL JEM-1011 Transmission Electron Microscopy (JEOL, Japan) operated at 80 kV with a Gatan digital camera (Gatan, USA). For the SEM analysis, a drop of diluted FMSN solution was deposited onto carbon tape, dried at 60° C., and sputtered with gold. The materials were analyzed using JEOL JSM-6700F Field Emission Scanning Electron Microscopy (JEOL, Japan).

Cell Culture.

Human pancreatic cancer cell line, PANC-1, and hepatoma cell line, Hepa-1, obtained from the American Type Culture Collection were cultured in Dulbecco's modified Eagle's medium (DMEM) supplemented with 10% fetal calf serum (Sigma), 2% L-glutamine, 1% penicillin, and 1% streptomycin stock solutions, incubated at 37° C. under a 5% $CO_2$ 95% air atmosphere. The media were changed every 3 days, and the cells were passaged by trypsinization before confluence.

Fluorescence and Confocal Microscopy.

The fluorescence of FITC was used to monitor cellular uptake of FMSN. Cells were incubated with FMSN for 3 h at 37° C. under a 5% $CO_2$ 95% air atmosphere in an 8-chamber Lab-Tek chamber slide system with covers (Nalge Nunc International), washed with phosphate buffered saline (PBS) and examined with confocal microscopy $\lambda_{ex}$=470 nm) (Carl Zeiss LSM 310 Laser Scanning Confocal microscopy). To examine the distribution of FMSN within the cells, the same cells were then incubated with 6 µM of Acridine Orange (AO) (Sigma), which specifically stains lysosomes/endosomes to red (Canonico, P. G. and Bird, J. W. C. (1969), *J. Cell Biol.* 43, 367-371), for 1 h in DMEM without phenol red, washed with PBS, and examined by confocal microscopy again ($\lambda_{ex}$=488 nm). The emission light was passed through a 560-nm short-pass dichroic mirror. The green emission was passed through a 530-nm bandpass filter, and the red emission was passed through a 600-nm longpass filter. Both emissions were simultaneously collected using two photomultiplier tubes.

Immunocytochemistry.

Cells cultured in chamber slides were also labeled for the location of lysosomes according to standard immunocytochemistry procedures. Briefly, after treating with FMSN for 3 h, cells were fixed, permeabilized, and blocked before antibody labeling. To label LAMP1 (Lysosome associated membrane protein 1) (Chen, J., Cha, Y., Yuksel, K., Gracy, R. and August, J. (1988), *J. Biol. Chem.* 263, 8754-8758), we used a rat anti-mouse monoclonal antibody (1D4B) (Abcam, Cambridge, Mass.). Primary antibody was incubated with the cells for 1 h at room temperature, and then a 1:500 dilution of secondary antibody (Alexa-594 goat anti-rat IgG, Molecular Probes, Eugene, Oreg.) was incubated at for 1 h at room temperature. Slides were mounted in Prolong anti-fade medium containing DAPI as counterstain (Molecular Probes), and then examined with confocal microscopy.

Cell Treatment and Confocal Microscopic Analysis.

To determine whether the uptake of FMSN into cancer cells was energy-dependent, the cells were incubated with FMSN under different metabolic conditions. The uptake assay was performed in the presence of sodium azide, sucrose, bafilomycin A, nocodazole or brefeldin A. Cells were seeded on 8-chamber Lab-Tek chamber slides for 24 h, then preincubated at 4° C. with either 0.1% sodium azide, or sucrose (0.45 M), or bafilomycin A (0.05 µM), or nocodazole (2 µg/ml), or brefeldin A (5 µg/ml) for 10 min. The FMSN suspension in PBS was then added and the cells were incubated for additional 3 h at 37° C. The uptake was stopped by washing the cells three times with cold PBS, and then the cells were fixed with 4% paraformaldehyde in PBS for 1 h at room temperature and washed with PBS. The chambers of slides were removed, and each slide was mounted with fluorescence-free glycerol-based mounting medium (Fluoromount-G; Southern Biotechnology Associates, USA) by cover glasses. Cells were analyzed by confocal microscopy (Carl Zeiss LSM 310 Laser Scanning Confocal microscopy).

Loading Anticancer Drug in the Pores of FMSN.

To load the paclitaxel drug molecules into the pores of the nanoparticles, 25 mg of FMSN were soaked in a solution containing 1 mg paclitaxel (Sigma-Aldrich, USA) and 2 mL DMSO. After 24 h, the mixture was centrifuged and the supernatant was removed completely. The paclitaxel-loaded FMSN was dried under vacuum to remove trace DMSO. The paclitaxel-loaded FMSN were washed and sonicated with PBS two times, and the supernatants were collected for absorbance measurement. The concentration of paclitaxel in the supernatants that represents weakly adsorbed drug molecules was calculated by measuring the absorbance of paclitaxel at 273 nm. To measure the amount of paclitaxel that is stored inside FMSN, the paclitaxel-loaded FMSN were then resuspended in methanol and sonicated thoroughly to remove the paclitaxel from the pores of FMSN (paclitaxel has high solubility in methanol). After centrifugation, the supernatant was collected and the process was repeated two more times to completely remove the drug from the pores of FMSN. The concentration of paclitaxel in the supernatant was calculated by measuring the absorbance of paclitaxel at 273 nm. The amount of paclitaxel adsorbed outside of FMSN was less than 5% of the amount that was stored inside FMSN.

Cell Growth Assay.

Cells were cultured in 96-well plates (3000 cells/well) with fresh DMEM at 37° C. in a 5% $CO_2$/95% air atmosphere for 24 h, then washed with PBS and the medium was changed to a fresh medium along with paclitaxel in DMSO, paclitaxel-loaded FMSN in PBS, unloaded FMSN or paclitaxel suspended in PBS at the indicated concentrations. 24 h later, the cells were washed with PBS to remove paclitaxel and FMSN that were not taken up by the cells and continued incubating in DMEM for an additional 48 h. 10% WST-8 solution (cell counting kit-8, Dojindo Molecular Technologies, Inc.) was then added to cells and incubated for another 2 h. The absorbance of each well was measured at 450 nm with a plate reader. Since the absorbance is proportional to the number of viable cells in the medium, the viable cell number was determined using a prepared calibration curve.

Cell Morphology Analysis.

Cells were seeded in 8-chamber Lab-Tek chamber for 24 h, washed with PBS, and then the medium was changed to a fresh medium along with paclitaxel in DMSO, paclitaxel-loaded FMSN in PBS, FMSN or paclitaxel suspended in PBS at the indicated concentrations. After 24 h, the medium was changed to fresh DMEM and incubation was continued for an additional 24 h. The cells were then washed with PBS and analyzed by light microscopy.

Statistical Analysis.

All results are expressed as means±SD. Statistical comparisons were made using Student's t-test after analysis of variance. The results were considered to be significantly different at P value<0.05.

Results and Discussion

Characteristics and Cellular Uptake of FMSN.

Mesoporous silica nanoparticles provide a promising vehicle to deliver anticancer drugs to cancer cells. The nanoparticles used in this study were less than 130 nm in diameter and contained pores that were around 2 nm in diameter. Approximately 750 pores are present per particle. FIGS. 18A and 18B show electron microscopy analysis of the morphology of the nanoparticles and the hexagonal arrays of the pores. FITC dyes were covalently bonded within the pores of the nanoparticles to enable the monitoring of FMSN by using fluorescent microscopy. In addition, the surface of FMSN was modified with inert and hydrophilic phosphonate group to prevent aggregation caused by the interparticle hydrogen bonding interaction between the anionic silanol groups and the unreacted cationic amine groups. Preparation of FMSN is described in the Experimental section and in our previous publication (Lu, J., Liong, M., Zink, J. I. and Tamanoi, F. (2007), *Small* 3, 1341-1346).

Figures 19A, 19B:
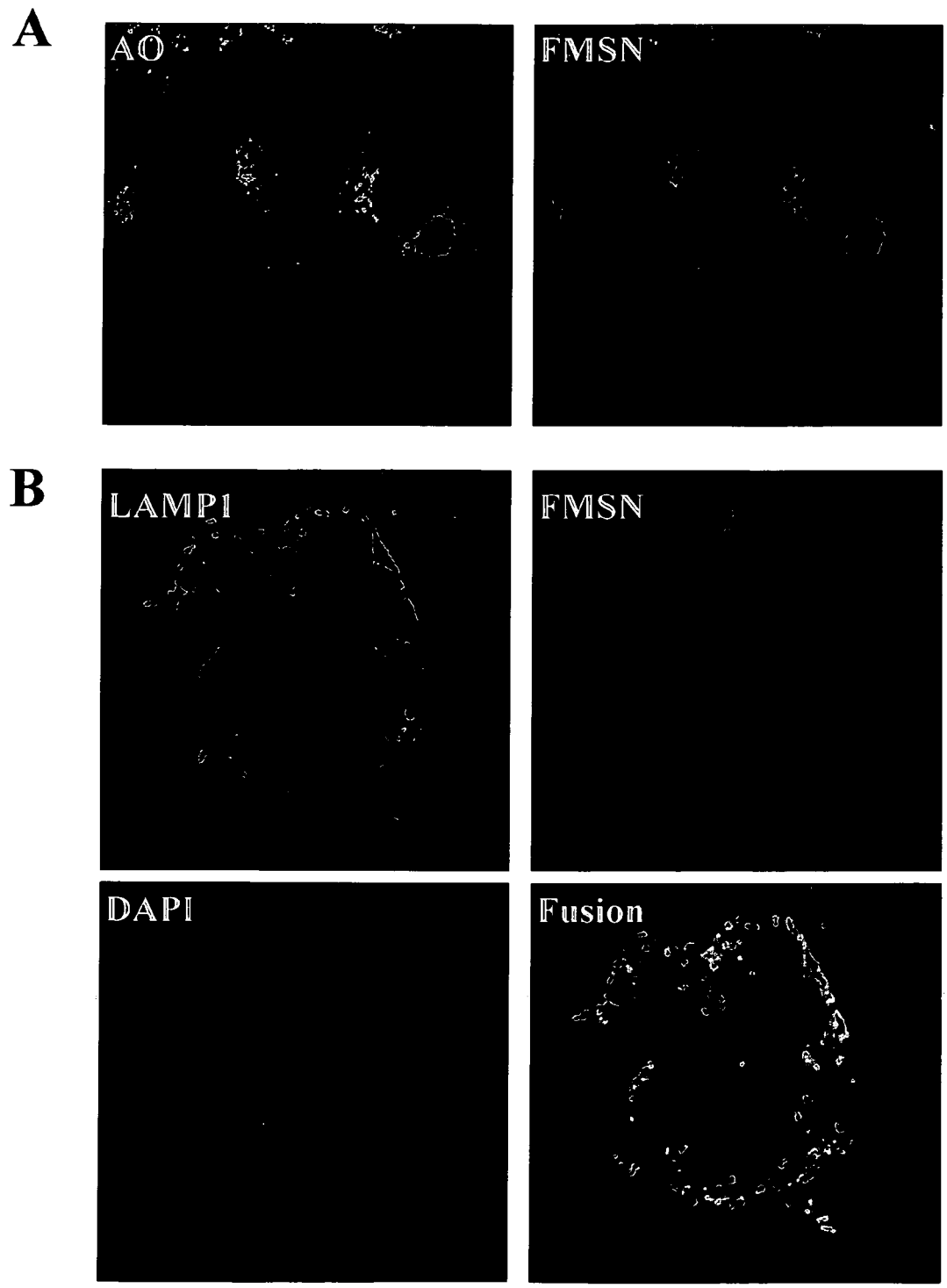
FIGS. 19A and 19B show uptake of FMSN by cancer cells.

Uptake of FMSN by cancer cells was observed using confocal microscopy. Cancer cells were incubated with FMSN and then washed with PBS to remove nanoparticles that were outside the cell. The fluorescence of the nanoparticles, which were derivatized with fluorescein, was monitored by confocal microscopy. FIG. 19 shows intracellular location of FMSN in PANC-1 (A) and Hepa-1 cells (B). PANC-1 cells were treated with FMSN followed by staining with Acridine orange. This dye specifically stains lysosomes red and the whole cell green (FIG. 19A left panel). Location of FMSN was identified by their green fluorescence (FIG. 19A right panel). As shown in FIG. 19A, the green fluorescence of FMSN overlapped with the red fluorescence of Acridine Orange, indicating that FMSN are taken into lysosomes shortly after they are taken up by cells. Similar results were observed in Hepa-1 cells as shown in FIG. 19B.

In this case, we used an antibody against LAMP1 (lysosome associated membrane protein 1) to detect lysosomes. Red fluorescence from LAMP1 in Hepa-1 cells overlapped with the green fluorescence from FMSN, resulting in a yellow composite staining pattern as shown in FIG. 19B (Fusion).

Energy-Dependent Endocytosis of FMSN by Cells.

Figure 21:
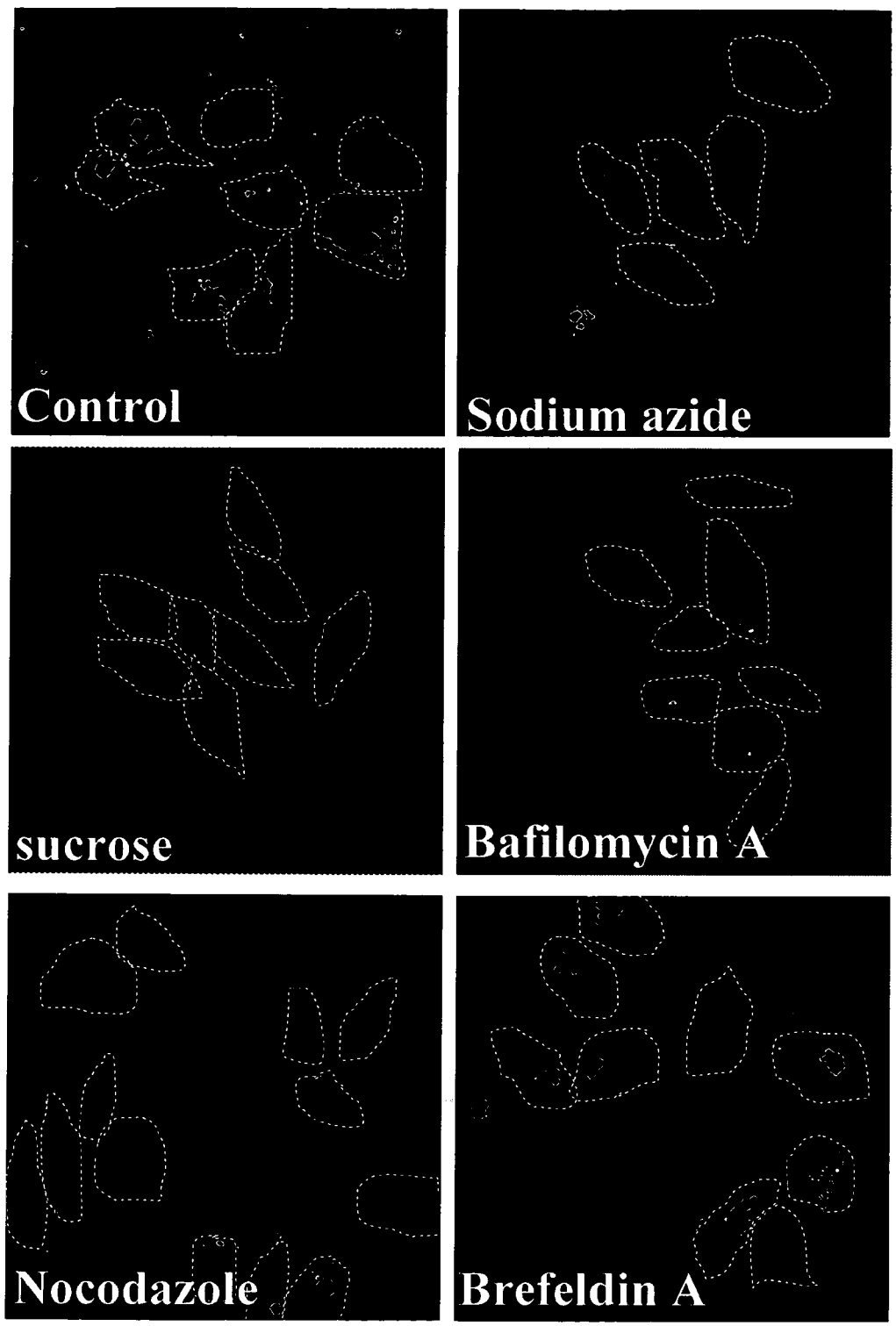
FIG. 21 shows confocal microscopy images of FMSN uptake in the presence of several metabolic inhibitors. PANC-1 cells were preincubated with metabolic inhibitors at the concentration indicated in the Experimental section and were then incubated with FMSN at 37° C. for 1 h. Cells were fixed and observed with confocal microscopy. Nuclei were stained with DAPI.

A number of processes including phagocytosis and endocytosis could account for the uptake of nanoparticles into cells. To further characterize the mechanism of uptake of FMSN, the cells were first incubated with FMSN at 37° C. or 4° C. As shown in FIG. 20, the lower temperature (4° C.) significantly impeded cellular uptake of FMSN in PANC-1 cells, compared with the uptake at 37° C. This result raised the possibility that FMSN enter cells in an energy-dependent manner. To further investigate this point, effects of different metabolic inhibitors on the uptake of FMSN into cells were examined. The cells were incubated with several metabolic inhibitors, such as sodium azide (Lichstein, H. C. and Soule, M. H. (1944), *J. Bacteriol.* 47, 231-238), sucrose (Heuser, J. E. and Anderson, R. G. (1989), *J. Cell Biol.* 108, 389-400), and bafilomycin A (Wessing, A., Bertram, G. and Zierold, K. (1993), *J. Comp. Physiol.* 163, 452), FMSN were added and the cells were cultured. Uptake of FMSN was examined using confocal microscopy. As shown in FIG. 21, preincubation with different metabolic inhibitors, including sodium azide (which depletes intracellular ATP), sucrose (which suppresses coated pit function), and bafilomycin A (which inhibits the v-ATPase function), suppressed the uptake of FMSN into PANC-1 cells. Sodium azide is widely used as an inhibitor of cellular respiration, decreasing intracellular ATP concentration. Thus, its inhibition of the uptake of FMSN suggested that the uptake was an energy-dependent process. Clathrin-coated pits are the primary plasma membrane location (Pearse, B. M. and Crowther, R. A. (1987), *Annu. Rev. Biophys. Biophys. Chem.* 16, 49-68) involved in the uptake of molecules through endocytosis. The hypertonic environment induced by sucrose, which disrupts coated pit function, impeded FMSN uptake, suggesting that the uptake process involved clathrin-mediated endocytosis. The proton pump vacuolar ATPase (V-ATPase) energizes plasma membranes in mammalian cells (Harvey, W. R., Maddrell, S. H. P., Telfer, W. H. and Wieczorek, H. (1998), *Amer. Zool.* 38, 426-441). Pretreatment with bafilomycin A which is a strong V-ATPase inhibitor completely suppressed the uptake of FMSN, indicating that the uptake occurred through a V-ATPase-dependent transport mechanism.

To investigate the effect of other endocytosis inhibitors, the microtubule depolymerizer nocodazole (Samson, F., Donoso, J. A., Heller-Bettinger, I., Watson, D. and Himes, R. H. (1979), *J. Pharmacol. Exp. Ther.* 208, 411-417) or the plasma membrane polarity inhibitor brefeldin A (Roma, M. G., Milkiewicz, P., Elias, E. and Coleman, R. (2000), *Hepatology* 32, 1342-1356) was preincubated with PANC-1 cells before the addition of FMSN. As shown in FIG. 21, while brefeldin A did not show any effect on FMSN uptake, nocodazole significantly disrupted the uptake, suggesting that a dynamic microtubule network, which is important for vesicular transport, is necessary for FMSN uptake.

Significance of the energy-dependent endocytosis on the uptake of silica-based nanoparticles has been reported with silica nanoparticles that are different from the FMSN used in this study. Chung T H et al. (Chung, T. H., Wu, S. H., Yao, M., Lu, C. W., Lin, Y. S., Hung, Y., Mou, C. Y., Chen, Y. C. and Huang, D. M. (2007), *Biomaterials* 28, 2959-2966) reported an actin-dependent endocytosis of mesoporous silica nanoparticles in 3T3-L1 cells. Using the organic fluorescent dye, rhodamine B, Kim et al. (Kim, J. S., Yoon, T. J., Yu, K. N., Noh, M. S., Woo, M., Kim, B. G., Lee, K. H., Sohn, B. H., Park, S. B., Lee, J. K. and Cho, M. H. (2006), *J. Vet. Sci.* 7, 321-326) showed that silica-overcoated magnetic nanoparticles were taken up by A549 cells through energy-dependent endocytosis. Gemeinhart et al. (Gemeinhart, R. A., Luo, D. and Saltzman, W. M. (2005), *Biotechnol. Prog.* 21, 532-537) reported that dense silica nanoparticles were internalized by an endosome-lysosomal route in Chinese hamster ovarian cells. Xing et al. (Xing, X., He, X., Peng, J., Wang, K. and Tan, W. (2005), *J. Nanosci. Nanotechnol.* 5, 1688-1693) used rhodamine 6G isothiocyanate (RITC)-doped silica-coated nanoparticles to show an energy-dependent endocytic process by HeLa cells. Taken together, these studies demonstrated the importance of temperature and energy-dependent endocytosis in the uptake of FMSN into human cancer cells.

Delivery of Hydrophobic Anticancer Drug Paclitaxel to Cancer Cells by FMSN.

Figure 22A:
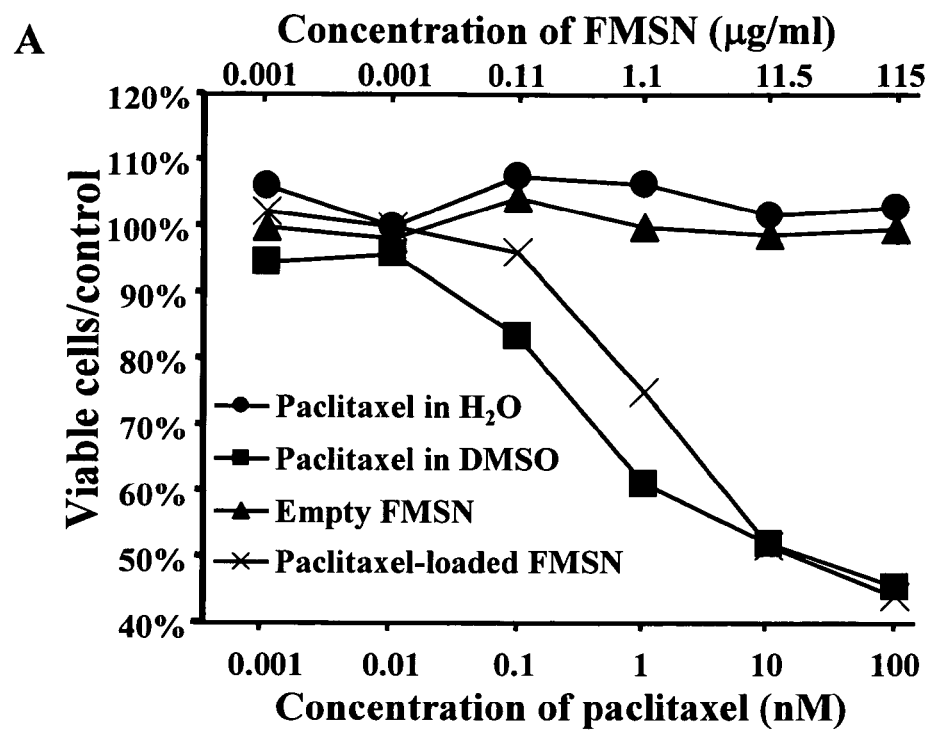
FIGS. 22A and 22B show cell growth inhibition assay.
Figure 22B:
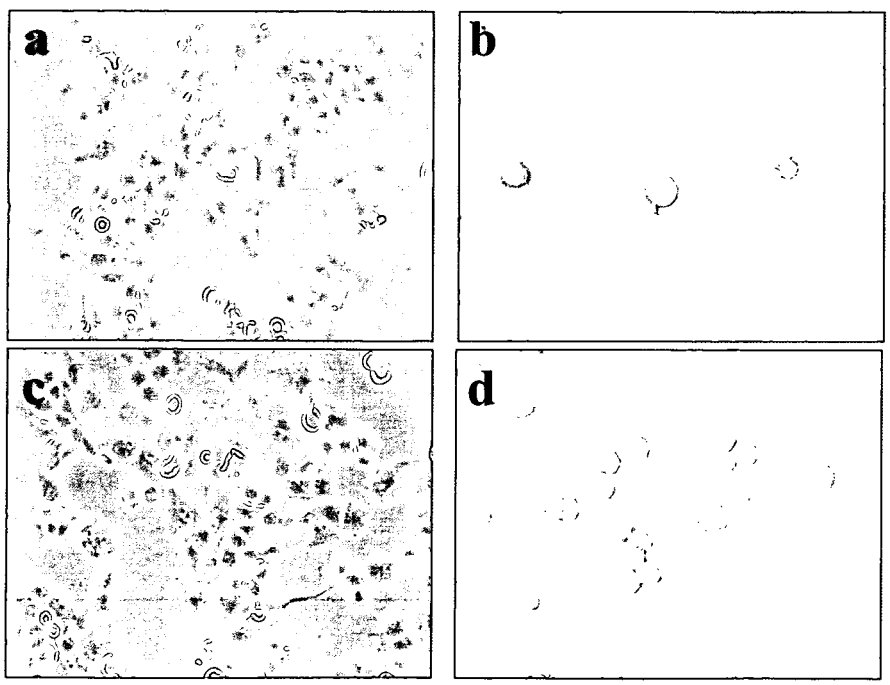

Many anticancer drugs have poor water solubility, which hampers the ability of drugs to be administered via the intravenous route. Therefore, development of novel delivery systems for these drugs without resorting to the use of organic solvents is critical for cancer therapy. We have previously used FMSN to deliver a hydrophobic anticancer agent camptothecin into cancer cells to induce apoptosis (Lu, J., Liong, M., Zink, J. I. and Tamanoi, F. (2007), *Small* 3, 1341-1346). To investigate whether this can be applied to other drugs, we have tested whether another hydrophobic drug paclitaxel can be delivered to cancer cells by FMSN. By soaking FMSN in a concentrated paclitaxel/DMSO solution, the drug molecules can enter the pores. After the organic solvent was removed by centrifugation and high vacuum, the hydrophobic drugs would be retained inside the pores. Because delivering paclitaxel into cancer cells is expected to lead to growth inhibition and cell death (Wani, M. C., Taylor, H. L., Wall, M. E., Coggon, P. and McPhail, A. T. (1971), *J. Am. Chem. Soc.* 93, 2325-2327), the cytotoxic effects of paclitaxel-loaded FMSN was examined. Growth inhibition of PANC-1 cells was observed with the cells treated with the suspension of paclitaxel-loaded FMSN in PBS. The extent of inhibition was comparable to that observed using paclitaxel dissolved in DMSO (FIG. 22A). In addition, we observed morphologic change of the cells treated with paclitaxel-loaded FMSN in PBS or paclitaxel dissolved in DMSO. Cells became round and smaller upon the treatment (FIG. 22B). These results are consistent with the effects of paclitaxel, which hyperstabilizes microtubule structure and causes morphologic changes in addition to its growth inhibitory effects.

As shown in FIG. 22A, empty FMSN did not cause inhibition of proliferation of PANC-1 cells. Also, we did not observe any cytotoxic effects of FMSN with other pancreatic cancer cell lines Capan-1 and AsPc-1, a colon cancer cell line SW480 and a stomach cancer cell line MKN45 (Lu, J., Liong, M., Zink, J. I. and Tamanoi, F. (2007), *Small* 3, 1341-1346). In addition, FMSN did not cause cytotoxic effects in a macrophage cell line RAW264.7 (data not shown), in contrast to other nanoparticles such as ZnO and cationic nanospheres that cause cytotoxic effects. These results suggest that the mesoporous silica nanoparticles themselves are not toxic to cultured mammalian cells. Other studies also point to biocompatibility of silica nanoparticles in human cells (Slowing, I., Trewyn, B. G. and Lin, V. S. (2006), *J. Am. Chem. Soc.* 128, 14792-14793; Luo, D. and Saltzman, W. M. (2000), *Nat. Biotechnol.* 18, 893-895; Jin, Y., Kannan, S., Wu, M. and Zhao, J. X. (2007), *Chem Res Toxicol*).

Together with our previous example demonstrating the successful loading of camptothecin and delivery into pancreatic cancer cells, FMSN have now been shown to serve as a delivery vehicle for two representative hydrophobic anticancer drugs, camptothecin and paclitaxel. However, the concepts of the current invention are not limited to only these particular examples. Because the low water solubility of anticancer drugs is frequently encountered in the development of effective therapy for cancer, our studies suggest that the mesoporous silica nanoparticles offer a solution to this problem in drug development.

In this example according to an embodiment of the current invention, we have shown that fluorescent mesoporous nanoparticles (FMSN) are efficiently taken up by human cancer cells and that this cellular uptake requires energy use and temperature-dependent endocytosis. Work is ongoing to further define the endocytosis pathway utilized by the nanoparticles. We have also shown that a hydrophobic anticancer drug paclitaxel can be stored in FMSN and delivered to human cancer cells resulting in the inhibition of proliferation of these cells. These results point to the useful feature of FMSN as a valuable vehicle for anticancer drugs. We are currently attaching nanovalves to FMSN so that the stored anticancer drugs can be released in a controlled manner. We believe the utilization of FMSN will provide a promising avenue for the development of an effective delivery system for cancer therapy.

The embodiments illustrated and discussed in this specification are intended only to teach those skilled in the art the best way known to the inventors to make and use the invention. Figures are not drawn to scale. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A submicron structure for delivering anticancer drugs into cancer cells, comprising:
    a silica body defining a plurality of pores, where said plurality of pores are suitable to receive anticancer molecules therein and to subsequently release said anticancer molecules therefrom, said silica body further defining an outer surface between pore openings of said plurality of pores; and
    a plurality of anionic molecules attached only to said outer surface of said silica body such that said plurality of pores are free of said plurality of anionic molecules thereby permitting said plurality of pores to receive anticancer molecules therein and to subsequently release said anticancer molecules therefrom;
    wherein said anionic molecules provide hydrophilicity to said submicron structure and are suitable to provide repulsion between other similar submicron structures; and
    wherein said submicron structure has a maximum dimension less than one micron.

2. A submicron structure according to claim 1, wherein said plurality of anionic molecules comprise a phosphonate moiety.

3. A submicron structure according to claim 1, wherein said plurality of anionic molecules are trihydroxysilylpropyl methylphosphonate.

4. A submicron structure according to claim 1, further comprising a nanoparticle of magnetic material formed within said silica body of said submicron structure.

5. A submicron structure according to claim 4, wherein said nanoparticle of magnetic material is an iron oxide nanoparticle.

6. A submicron structure according to claim 4, wherein said nanoparticle of magnetic material has a maximum dimension greater than about 5 nm and less than about 30 nm.

7. A submicron structure according to claim 1, further comprising a nanoparticle of gold formed within said silica body of said submicron structure.

8. A submicron structure according to claim 1, further comprising a plurality of folate ligands attached to said outer surface of said silica body of said submicron structure.

9. A submicron structure according to claim 1, further comprising a fluorescent molecule attached to said silica body of said submicron structure.

10. A submicron structure according to claim 9, wherein said fluorescent molecule attached to said silica body is an amine-reactive fluorescent dye attached by being conjugated with an amine-functionalized silane.

11. A submicron structure according to claim 10, wherein said fluorescent molecule is selected from the group consisting of fluorescein isothiocyanate, N-hydroxysuccinimide fluorescein (NHS-fluorescein), rhodamine B isothiocyanate, tetramethylrhodamine B isothiocyanate, and Cy5.5 NHS ester.

12. A composition for delivering anticancer drugs into cancer cells, said composition comprising a plurality of mesoporous silica nanoparticles, wherein each mesoporous silica nanoparticle of said plurality of mesoporous silica nanoparticles comprises:
    a silica body defining a plurality of pores, where said plurality of pores are suitable to receive anticancer molecules therein and to subsequently release said anticancer molecules therefrom, said silica body further defining an outer surface between pore openings of said plurality of pores; and
    a plurality of anionic molecules attached only to said outer surface of said silica body such that said plurality of pores are free of said plurality of anionic molecules such that said plurality of pores remain suitable to receive anticancer molecules therein and to subsequently release said anticancer molecules therefrom.

13. A composition according to claim 12, wherein said plurality of anionic molecules comprise a phosphonate moiety.

14. A composition according to claim 12, wherein said plurality of anionic molecules comprise trihydroxysilylpropyl methylphosphonate.

15. A composition according to claim 12, wherein each of said plurality of mesoporous silica nanoparticle comprises a core comprising a magnetic material.

16. A composition according to claim 12, wherein each of said plurality of mesoporous silica nanoparticle comprises a core comprising a material that is optically dense to x-rays.

17. A composition according to claim 12, wherein each of said plurality of mesoporous silica nanoparticle comprises a plurality of folate ligands attached thereto.

18. A composition according to claim 12, wherein said plurality of mesoporous silica nanoparticles has an ensemble average maximum dimension less than about 300 nm.

19. A composition according to claim 12, wherein said plurality of mesoporous silica nanoparticles has an ensemble average maximum dimension greater than about 50 nm and less than about 150 nm.

20. A submicron structure according to claim 1, wherein said plurality of pores contain hydrophobic anticancer molecules therein.

21. A composition according to claim 12, wherein said plurality of pores contain hydrophobic anticancer molecules therein.

22. A submicron structure according to claim 1, wherein said plurality of pores contain a drug selected from the group consisting of camptothecin, paclitaxel, resveratrol, etoposide, and carmustine.

23. A composition according to claim 12, wherein said plurality of pores contain a drug selected from the group consisting of camptothecin, paclitaxel, resveratrol, etoposide, and carmustine.

* * * * *